(12) United States Patent
Borgström

(10) Patent No.: US 9,132,105 B2
(45) Date of Patent: Sep. 15, 2015

(54) TREATMENT OF PROSTATE CARCINOMA

(75) Inventor: Per Borgström, La Jolla, CA (US)

(73) Assignee: Pellficure Pharmaceuticals, Inc., La Jolla, CA (US)

( * ) Notice: Subject to any disclaimer, the term of this patent is extended or adjusted under 35 U.S.C. 154(b) by 0 days.

(21) Appl. No.: 13/813,394

(22) PCT Filed: Aug. 3, 2011

(86) PCT No.: PCT/US2011/046474
§ 371 (c)(1),
(2), (4) Date: Mar. 27, 2013

(87) PCT Pub. No.: WO2012/018948
PCT Pub. Date: Feb. 9, 2012

(65) Prior Publication Data
US 2013/0219528 A1 Aug. 22, 2013

Related U.S. Application Data

(60) Provisional application No. 61/370,534, filed on Aug. 4, 2010.

(51) Int. Cl.
| | | |
|---|---|---|
| *A61K 31/122* | (2006.01) |
| *A61K 31/58* | (2006.01) |
| *A61K 38/09* | (2006.01) |
| *A61P 35/00* | (2006.01) |
| *A61K 31/05* | (2006.01) |
| *A61K 31/167* | (2006.01) |
| *A61K 31/277* | (2006.01) |
| *A61K 31/4166* | (2006.01) |
| *A61K 31/565* | (2006.01) |
| *A61K 31/57* | (2006.01) |
| *A61K 31/6615* | (2006.01) |
| *A61K 45/06* | (2006.01) |
| *G01N 33/50* | (2006.01) |

(52) U.S. Cl.
CPC ............. *A61K 31/122* (2013.01); *A61K 31/05* (2013.01); *A61K 31/167* (2013.01); *A61K 31/277* (2013.01); *A61K 31/4166* (2013.01); *A61K 31/565* (2013.01); *A61K 31/57* (2013.01); *A61K 31/58* (2013.01); *A61K 31/6615* (2013.01); *A61K 38/09* (2013.01); *A61K 45/06* (2013.01); *G01N 33/5011* (2013.01); *G01N 33/5088* (2013.01)

(58) Field of Classification Search
CPC ...... A61K 31/122; A61K 31/58; A61K 38/09
USPC ............. 514/682, 171, 681, 732, 10.3, 10.4, 514/19.5, 21.6
See application file for complete search history.

(56) References Cited

U.S. PATENT DOCUMENTS

2006/0111318 A1 5/2006 Okamoto
2007/0071787 A1 3/2007 Saffie et al.

FOREIGN PATENT DOCUMENTS

| CN | 1095275 A | 11/1994 |
|---|---|---|
| CN | 101037447 | 9/2010 |
| EP | 0173262 A2 | 3/1986 |
| WO | WO9200748 A1 | 1/1992 |
| WO | WO9833506 A1 | 8/1998 |
| WO | WO2004060402 A1 | 7/2004 |
| WO | WO2007147128 A2 | 12/2007 |
| WO | WO2009114525 A1 | 9/2009 |
| WO | WO2010091299 | 8/2010 |
| WO | WO2011082245 | 7/2011 |
| WO | WO2012018948 A2 | 2/2012 |
| WO | WO2012058529 | 5/2012 |
| WO | WO2012064943 | 5/2012 |
| WO | WO2012158884 | 11/2012 |
| WO | WO2014158875 A1 | 10/2014 |

OTHER PUBLICATIONS

Attard et al. J. Clin. Oncol. 2008, 26 (28), 4563-4571.*
Abedinpour et al., (Epub. Sep. 19, 2012) "The combination of plumbagin with androgen withdrawal causes profound regression of prostate tumors in vivo". The Prostate, 73(5):489-499, 2013.
Arumugam et al., "Preparation, in vitro characterization, pharmacokinetic, and pharmacodynamic evaluation of chitosan-based plumbagin microspheres in mice bearing B16F1 melanoma," Drug Delivery, 17(3):103-113, 2010.
Aziz et al., "Plumbagin, A Medicinal Plant-Derived Naphthoquinone, is a Novel Inhibitor of the Growth and Invasion of Hormone-Refractory Prostate Cancer," Cancer Res., 68(21):9024-9032, 2008.
Backman et al., "Early onset of neoplasia in the prostate and skin of mice with tissue-specific deletion of PTEN," Proc Natl Acad Sci, 101(6):1725-1730, 2004.
Bachur et al., "A General Mechanism for Microsomal Activation of Quinone Anticancer Agents to Free Radicals," Cancer Res., 38:1745-1750, 1978.
Bezerra et al., "Antitumor activity of two derivatives from 2-acylamine-1, 4-naphthoquinone in mice bearing S180 tumor," J Exp Ther Oncol, 7:113-21, 2008.

(Continued)

*Primary Examiner* — Sreeni Padmanabhan
*Assistant Examiner* — Irina Neagu
(74) *Attorney, Agent, or Firm* — Knobbe, Martens, Olson & Bear, LLP

(57) ABSTRACT

Disclosed herein are naphthoquinone analogs, such as plumbagin, pharmaceutical compositions that include naphthoquinone analogs, such as plumbagin, and methods of treating diseases and/or conditions such as cancer with naphthoquinone analogs, such as plumbagin. Also included are combination therapies wherein a naphthoquinone analog, such as plumbagin, and a hormone therapy agent are provided to a subject suffering from a condition such as cancer.

18 Claims, 8 Drawing Sheets

(56) References Cited

OTHER PUBLICATIONS

Hafeez et al., "Plumbagin a Non-Toxic Natural Agent, Induces Apoptosis and Inhibits the Growth of Prostate Cancer LNCaP and C4-2 Cells Via Blocking of Both Androgen and Non-Androgen Activation of Androgen Receptor Signaling", Proceedings of the American Association for Cancer Research Annual Meeting, 51:919, #3780.
Blanco-Aparicio et al., "PTEN, More than the AKT Pathway," Carcinogenesis, 28:1379-1386, 2007.
Boothman et al., "Potentiation of Halogenated Pyrimidine Radiosensitizers in Human Carcinoma Cells by β-Lapachone (3,4-Dihydro-2,2-dimethyl-2$H$-naphtho[1,2-$b$]pyran-5,6-dione), a Novel DNA Repair Inhibitor," Cancer Res., 47:5361-66, 1987.
Bubendorf et al., "Metastatic Patterns of Prostate Cancer: An Autopsy Study of 1,589 Patients," Hum. Pathol., 31(5):578-583, 2000.
Chae et al., "2- or 6-(1-azidoalkyl)-5,8-dimethoxy-1,4-naphthoquinone: synthesis, evaluation of cytotoxic activity, antitumor activity and inhibitory effect on DNA topoisomerase-I," Arch Pharm Res, 22(5):507-514, 1999.
Chalhoub et al., "PTEN and the PI3-Kinase Pathway in Cancer," Annu Rev Pathol, 4:127-150, 2009.
Chiles et al., "Relationships of Testosterone and Prostate Cancer: A 2011 Perspective," Renal & Urology News, May 1, 2011.
Copeland et al., "Cytotoxicity of 2,3-Dichloro-5,8-Dimethoxy-1,4-Naphthoquinone in Androgen-Dependent and -Independent Prostate Cancer Cell Lines," Anticancer Research, 27(3B):1537-1546, 2007.
Da Consolacao et al., "A Lapachol derivative active against mouse lymphocytic leukemia P-388," J Med Chem, 18(11):1159-1161, 1975.
Deocampo et al., "The Role of PTEN in the Progression and Survival of Prostate Cancer," Minerva Endocrinol, 28:145-153, 2003.
Di Cristofano et al., "The Multiple Roles of PTEN in Tumor Suppression," Cell, 100:387-390, 2000.
Frew et al., "Novel quinone antiproliferative inhibitors of phosphatidylinositol-3-kinase," Anticancer Drug Des, 10:347-359, 1995.
Frost el al., "Real Time in Vivo Quantitation of Tumor Angiogenesis," Methods Mol Med, 85:65-78, 2003.
Frost et al., "Novel Syngeneic Pseudo-Orthotopic Prostate Cancer Model: Vascular, Mitotic and Apoptotic Responses to Castration," Microvasc Res, 69:1-9, 2005.
Ghosh et al., "Synthesis of plumbagin derivatives and their inhibitory activities against Ehrlich ascites carcinoma in vivo and Leishmania donovani promastigotes in vitro," Phytotherapy Research, 16(52):133-137, 2002.
Gilloteaux et al., "Scanning Electron Microscopy and Transmission Electron Microscopy Aspects of Synergistic Antitumor Activity of Vitamin C-Vitamin K3 Combinations Against Human Prostatic Carcinoma Cells," Scanning Microscopy, 9(1):159-173, 1995.
Hasegawa et al., Jan. 1, 2013, "Effect of Polyphenols on Production of Steroid Hormones from Human Adrenocortical NCI-H295R Cells", Biological & Pharmaceutical Bulletin, 36(2):228-237.
International Search Report and Written Opinion for PCT/US2014/020637 dated Aug. 25, 2014.
Jacoby et al., Feb. 2013, "Differential effects of galeterone abiraterone, abiraterone, orteronel and ketoconazole on CYP 17 and steroidogenesis", Genitourinary Cancers Symposium. Urotoday. com. [retrieved from internet: www.urotoday.com/GU-Cancers-Symp,-2013-Prostate-Cancer/gu-cancers-symposium-2013-differential-effects-of-galeterone-abiraterone-orteronel-and-ketoconazole-on-cyp17-and-steroidogenesis-by-douglas-b-jacoby-et-al-session. html].
Jamison et al., "Evaluation of the In Vitro and In Vivo Antitumor Activities of Vitamin C and K-3 Combinations against Human Prostate Cancer," J Nutr, 131:158S-160S, 2001.
Jemal et al., "Cancer statistics, 2009," CA Cancer J Clin, 59:225-249, 2009.
Jiao et al., "Murine Cell Lines Derived from Pten Null Prostate Cancer Show the Critical Role of PTEN in Hormone Refractory Prostate Cancer Development," Cancer Res, 67:6083-6091, 2007.
Joyce et al., "High Dose Bicalutamide for Androgen Independent Prostate Cancer: Effect of Prior Hormonal Therapy," Journal of Urology, 159(1):149-153, 1998.
Kanda et al., "Histone-GFP Fusion Protein Enables Sensitive Analysis of Chromosome Dynamics in Living Mammalian Cells," Curr Biol, 8(7):377-85, 1998.
Krishnaswamy et al., "Plumbagin: a study of its anticancer, antibacterial and antifungal properties," Indian J. Exp. Biol., 18:876-877, 1980.
Kyong-Up et al., "2-Substituted Naphthazarins; Synthesis and Antitumor Activity," Arch Pharm, 330(12):377-382, 1997.
Matthew et al., "Inhibition of Mycobacterial Growth by Plumbagin Derivatives," Chemical Biology & Drug Design, 76(1):34-42, 2010.
Larsson et al., "Combination analyses of anti-cancer drugs on human neuroendocrine tumor cell lines," Cancer Chemother Pharmacol, 65:5-12, 2009.
Lasalvia-prisco et al., "Serum markers variation consistent with autoschizis induced by ascorbic acid-menadione in patients with prostate cancer," Med Oncol, 20(1):45-52, 2003.
Lee et al., "MAPK regulation and caspase activation are required in DMNQ S-52 induced apoptosis in Lewis lung carcinoma cell," Cancer Lett, 233:57-67, 2006.
Lehr et al., "Dorsal Skinfold Chamber Technique for Intravital Microscopy in Nude Mice," Am J Pathol, 143(4):1055-1062, 1993.
Lesche et al., "Cre/loxP Mediated Inactivation of the Murine Pten Tumor Suppressor Gene," Genesis, 32:148-149, 2002.
Leslie et al., "PTEN Function: How Normal Cells Control It and Tumour Cells Lose It," Biochem J, 382:1-11, 2004.
Lim et al., "Phase I trial of menadiol diphosphate (vitamin $K_3$) in advanced malignancy," Invest New Drugs, 23(3):235-239, 2005.
Lund et al., (Epub. Dec. 17, 2003), "Equol is a Novel Anti-Androgen that Inhibits Prostate Growth and Hormone Feedback", Biology of Reproduction, 70(4):1188-1195, 2004.
Maeda et al., "Promotion or suppression of experimental metastasis of B16 melanoma cells after oral administration of lapachol," Toxicol Appl Pharmacol, 229:232-238, 2008.
Majumder et al., "Prostate Intraepithelial Neoplasia Induced by Prostate Restricted Akt Activation: The MPAKT Model," Proc Natl Acad Sci, 100(13):7841-7846, 2003.
Margolin et al., "Phase I study of mitomycin C and menadione in advanced solid tumors," Cancer Chemother Pharmocol, 36(4):293-298, 1995.
Mathur et al., "Peptidyl prolyl isomerase, Pin1 is a potential target for enhancing the therapeutic efficacy of etoposide," Curr Cancer Drug Targets, 11(3):380-392, 2011.
Mostaghel et al., "Castration-Resistant Prostate Cancer: Targeting Androgen Metabolic Pathways in Recurrent Disease," Urologic Oncology, 27(3):251-257, 2009.
Nakabayashi et al., "Efficacy of Nilutamide as Secondary Hormonal Therapy in Androgen-Independent Prostate Cancer," BJU International, 96(6):783-786, 2005.
Nanni et al., "P185(Neu) Protein is Required for Tumor and Anchorage-Independent Growth, Not for Cell Proliferation of Transgenic Mammary Carcinoma," Int J Cancer, 87:186-194, 2000.
Narimoto et al., "Adrenal Androgen Levels as Predictors of Outcome in Castration-Resistant Prostate Cancer Patients Treated with Combined Androgen Blockade Using Flutamide as a Second-Line Anti-Androgen," International Journal of Urology, 17(4):337-345, 2010.
Nemoto et al., "Activation of the Raf-1/MEK/Erk kinase pathway by a novel Cdc25 inhibitor in human prostate cancer cells," The Prostate, 58(1):95-102, 2004.
Nimptsch et al., "Dietary vitamin K intake in relation to cancer incidence and mortality: results from the Heidelberg Cohort of the European Prospective Investigation into Cancer and Nutrition (EPIC-Heidelberg)," Am J Clin Nutr, 91:1348-58, 2010.
Noda et al., "Cytotoxicity of Naphthoquinones toward Cultured Resting Murine Leukemia L1210 Cells in the Presence of Glutathione, Diethyl Maleate, or Iodoacetamide," Biological & Pharmaceutical Bulletin, 20(12):1250-1256, 1997.

(56) References Cited

OTHER PUBLICATIONS

O'Brien, "Molecular mechanisms of quinone cytotoxicity," Chem Biol. Interact, 80:1-41, 1991.
Parimala et al., "Effect of Plumbagin on some glucose metabolising enzymes studied in rats in experimental hepatoma," Mol. Cell. Biochem, 125(1):59-63, 1993.
Phillips et al., "Pharmacological and biological evaluation of a series of substituted 1,4-naphthoquinone bioreductive drugs," Biochemical Pharmacology, 68(11):2107-2116, 2004.
Powolny et al., "Plumbagin-induced Apoptosis in Human Prostate Cancer Cells is Associated with Modulation of Cellular Redox Status and Generation of Reactive Oxygen Species," Pharmaceutical Research, 25(9):2171-2180, 2008.
Simpson et al., "PTEN: Life as a Tumor Suppressor," Exp Cell Res, 264:29-41, 2001.
Song et al., "Naphthazarin derivatives (VII): Antitumor action against ICR mice bearing ascitic S-180 cells," Arch Pharm Res, 24(3):190-193, 2001.
Sugie et al., "Inhibitory effects of plumbagin and juglone on azoxymethane-induced intestinal carcinogenesis in rats," Cancer Lett, 127(1-2):177-183, 1998.
Talcott et al., "Inhibition of microsomal lipid peroxidation by naphthoquinones: structure-activity relationships and possible mechanisms of action," Archives of Biochemistry and Biophysics, 241(1):88-94, 1985.
Tareen et al., "A 12 Week, Open Label, Phase I/IIa Study Using Apatone® for the Treatment of Prostate Cancer Patients Who Have Failed Standard Therapy," Int J Med Sci, 5:62-67, 2008.
Tetef et al., "Mitomycin C and menadione for the treatment of lung cancer: a phase II trial," Invest New Drugs, 13:157-162, 1995.
Tetef et al., "Mitomycin C and menadione for the treatment of advanced gastrointestinal cancers: a phase II trial," J Cancer Res Clin Oncol, 121:103-106, 1995.
Tokunaga et al., "Cytotoxic Antifeedant from *Dionaea muscipula* Ellis: A Defensive Mechanism of Carnivorous Plants against Predators," Bulletin of the Chemical Society of Japan, 77(3):537-541, 2004.
Trotman et al., "PTEN Dose Dictates Cancer Progression in the Prostate," PLoS Biol, 1(3):385-396, 2003.
Vasanth et al., "Synthesis of some plumbagin derivatives and their antibacterial activity," Journal of the Indian Chemical Society, 81(6):509-510, 2004.

Vivanco et al., "The Phosphatidylinositol 3-Kinase AKT Pathway in Human Cancer," Nat Rev Cancer, 2:489-501, 2002.
Wang et al., "Prostate-Specific Deletion of the Murine PTEN Tumor Suppressor Gene Leads to Metastatic Prostate Cancer," Cancer Cell, 4:209-221, 2003.
Wu et al., "Generation of a Prostate Epithelial Cell-Specific Cre Transgenic Mouse Model for Tissue-Specific Gene Ablation," Mech Dev, 101:61-69, 2001.
Ye et al., "Inhibitors of testosterone biosynthetic and metabolic activation enzymes", Molecules, 16(12):9983-10001, 2001.
Zhu et al., "Treatment of Castration-Resistant Prostate Cancer: Updates on Therapeutics Targeting the Androgen Receptor Signaling Pathway," American Journal of Therapeutics, 17(2):176-181, 2010.
International Search Report and Written Opinion dated Jul. 4, 2012, issued in International Application No. PCT/US2011/046474, filed Aug. 3, 2011.
Patent Examination Report dated Nov. 27, 2013, issued in Australian Application No. 2011285724, filed Mar. 1, 2013.
EAU Guidelines on Prostate Cancer, Apr. 2010.
Loblaw et al., "Initial Hormonal Management of Androgen-Sensitive Metastatic, Recurrent, or Progressive Prostate Cancer: 2007 Update of an American Society of Clinical Oncology Practice Guideline," Journal of Clinical Oncology, 25:1596-1605, 2007.
Wetherill et al., "Bisphenol A facilitates bypass of androgen ablation therapy in prostate cancer," Molecular Cancer Therapeutics, 5:3181-3190, 2006.
Chinese Office Action for Chinese Patent Application No. 201180046484.8 dated Sep. 11, 2014.
Notice of Acceptance for Australian Patent Application No. 2011285724 dated Jan. 6, 2015.
Chen et al. "Efficacy of maximal androgen blockade versus castration alone in the treatment of advanced prostate cancer: a retrospective clinical experience from a Chinese medical centre." Asian Journal of Andrology (2010) 12: 718-727.
Chinese Office Action dated Apr. 27, 2015, issued in corresponding Chinese Application No. 201180046484.8, filed Mar. 27, 2013.
Eisenberger et al. "Bilateral Orchiectomy with or without Flutamide for Metastatic Prostate Cancer." New England Journal of Medicine. Oct. 1998. vol. 339, No. 15. 1036-1042.
Gomella, Leonard G. "Effective Testosterone Suppression for Prostate Cancer: Is There a Best Castration Therapy?" Reviews in Urology. (2009) vol. 11, No. 2. 52-60.
Korean Office Action dated Jun. 12, 2015, issued in corresponding Korean Application No. 10-2013-7005592, filed Mar. 4, 2013.

\* cited by examiner

TREATMENT OF PROSTATE CARCINOMA

CROSS-REFERENCE TO RELATED APPLICATIONS

This application is a U.S. National Phase Application of PCT International Application Number PCT/US2011/046474, filed on Aug. 3, 2011, designating the United States of America and published in the English language, which is an International Application of and claims the benefit of priority to U.S. Provisional Application No. 61/370,534, filed Aug. 4, 2010; which are hereby expressly incorporated by reference in their entireties.

FIELD OF THE INVENTION

Aspects of the present application relate to the fields of chemistry, biochemistry and medicine. More particularly, disclosed herein are naphthoquinone analogs, such as plumbagin, pharmaceutical compositions that include naphthoquinone analogs, such as plumbagin, and methods of treating diseases and/or conditions with naphthoquinone analogs, such as plumbagin. Also included are combination therapies, wherein a naphthoquinone analog, such as plumbagin, and a hormone therapy agent, such as a hormonal ablation compound, are provided to a subject having a cancer, such as a prostate cancer.

BACKGROUND OF THE INVENTION

Prostate cancer develops in the prostate and is typically slow growing; however, some prostate cancers are aggressive. Prostate cancer cells are typically androgen/testosterone/DHT dependent and may metastasize from the prostate to other parts of the body, particularly the bones and lymph nodes. Treatment options for prostate cancer that remains within the prostate include watchful waiting/active surveillance, external beam radiation therapy, brachytherapy, cryosurgery, HIFU, and surgery. Hormonal therapy and chemotherapy are often reserved for disease that has spread beyond the prostate. However, there are exceptions in that radiation therapy may be used for some advanced tumors, and hormonal therapy may be used for some early stage tumors.

After one to three years of hormonal therapy, it is common that prostate cancer cells resume growth despite the androgen/testosterone/DHT blockade. Previously referred to as "hormone-refractory prostate cancer" or "androgen-independent prostate cancer," the term castration-resistant prostate cancer (CRPC) is now commonly used. Chemotherapeutic agents and immunotherapy have been shown to prolong survival after CRPC but the survival benefit is limited. Despite the efforts of many, the need for more cancer treatments, in particular prostate cancer treatments, is manifest.

SUMMARY

Some embodiments disclosed herein relate to a method of inhibiting or delaying the growth of prostate cancer by providing a subject having prostate cancer with a therapeutically effective amount of a compound of Formula (I), or a pharmaceutically acceptable salt of Formula (I), while reducing the amount of an androgen in the subject. In some embodiments, the amount of androgen can be reduced by providing the subject with an anti-androgen compound, an estrogen, a luteinizing hormone-releasing hormone (LHRH) agonist, or a LHRH antagonist. In some embodiments, the amount of androgen can be reduced by providing the subject with a steroidal anti-androgen or a non-steroidal anti-androgen. In some embodiments, the amount of androgen can be reduced by providing the subject with cyproterone acetate, abiraterone, finasteride, flutamide, nilutamide, bicalutamide, ethylstilbestrol (DES), megestrol acetate, fosfestrol, estamustine phosphate, leuprolide, triptorelin, goserelin, histrelin, buserelin, abarelix and/or degarelix. In some embodiments, the method of inhibiting or delaying the growth of prostate cancer can reduce the subject's serum testosterone level to between about 20-50 ng/dL. In some embodiments, the method of inhibiting or delaying the growth of prostate cancer can reduce the subject's serum testosterone level to less than about 50 ng/dL. In some embodiments, the method of inhibiting or delaying the growth of prostate cancer can reduce the subject's serum testosterone level to less than about 20 ng/dL.

Some embodiments disclosed herein relate to a method for identifying a compound that inhibits or delays prostate cancer cell growth by providing a pseudo-orthotopic chamber mouse model, wherein the mouse model has prostate cancer; reducing the level of an androgen in said mouse model; providing the mouse model with a compound of Formula (I) or a pharmaceutically acceptable salt or a prodrug thereof; and evaluating whether the compound is effective in inhibiting the growth of prostate cancer cells.

Some embodiments disclosed herein relate to a method of inhibiting or delaying the onset of castration-resistant prostate cancer (CRPC) by classifying a subject as a member of a population that is at risk for developing CRPC; providing said subject with a therapeutically effective amount of a compound of Formula (I), or a pharmaceutically acceptable salt of Formula (I), while reducing the amount of an androgen in said subject; and evaluating an inhibition or delay of prostate cancer cell growth or a marker thereof or the onset of CRPC.

Some embodiments disclosed herein relate to a method of identifying a compound that inhibits or delays prostate cancer cell growth by contacting prostate cancer cells with a compound of Formula (I) in the absence of androgen; determining the presence or absence of an inhibition or delay in prostate cancer cell growth; and classifying the compound into a population that inhibits or delays prostate cancer cell growth in the absence of androgen, or into a population that does not inhibit or delay prostate cancer cell growth.

Some embodiments disclosed herein relate to a method of making a prostate cancer therapeutic by contacting prostate cancer cells with a compound of Formula (I) in the absence of androgen; determining the presence or absence of an inhibition or delay in prostate cancer cell growth; selecting a compound of Formula (I) that inhibits prostate cancer cell growth in the absence of androgen; and formulating the compound that inhibits or delays prostate cancer cell growth in the absence of androgen for administration to a subject suffering from prostate cancer.

Some embodiments disclosed herein relate to a combination of a compound of Formula (I) or a pharmaceutically acceptable salt of Formula (I) and a hormone therapy agent for inhibiting or delaying prostate cancer cell growth or the onset of castration-resistant prostate cancer (CRPC). In some embodiments, the hormone therapy agent can be cyproterone acetate, abiraterone, finasteride, flutamide, nilutamide, bicalutamide, ethylstilbestrol (DES), megestrol acetate, fosfestrol, estamustine phosphate, leuprolide, triptorelin, goserelin, histrelin, buserelin, abarelix or degarelix or any combination of one or more of said compounds.

Some embodiments disclosed herein relate to a combination of a compound of Formula (I) or a pharmaceutically acceptable salt of Formula (I) and a hormone therapy agent for use in decreasing prostate tumor size. In some embodiments, the hormone therapy agent can be cyproterone acetate, abiraterone, finasteride, flutamide, nilutamide, bicalutamide, ethylstilbestrol (DES), megestrol acetate, fosfestrol, estamustine phosphate, leuprolide, triptorelin, goserelin, histrelin, buserelin, abarelix or degarelix or any combination of one or more of said compounds.

DETAILED DESCRIPTION

I. Definitions

Figure 1:
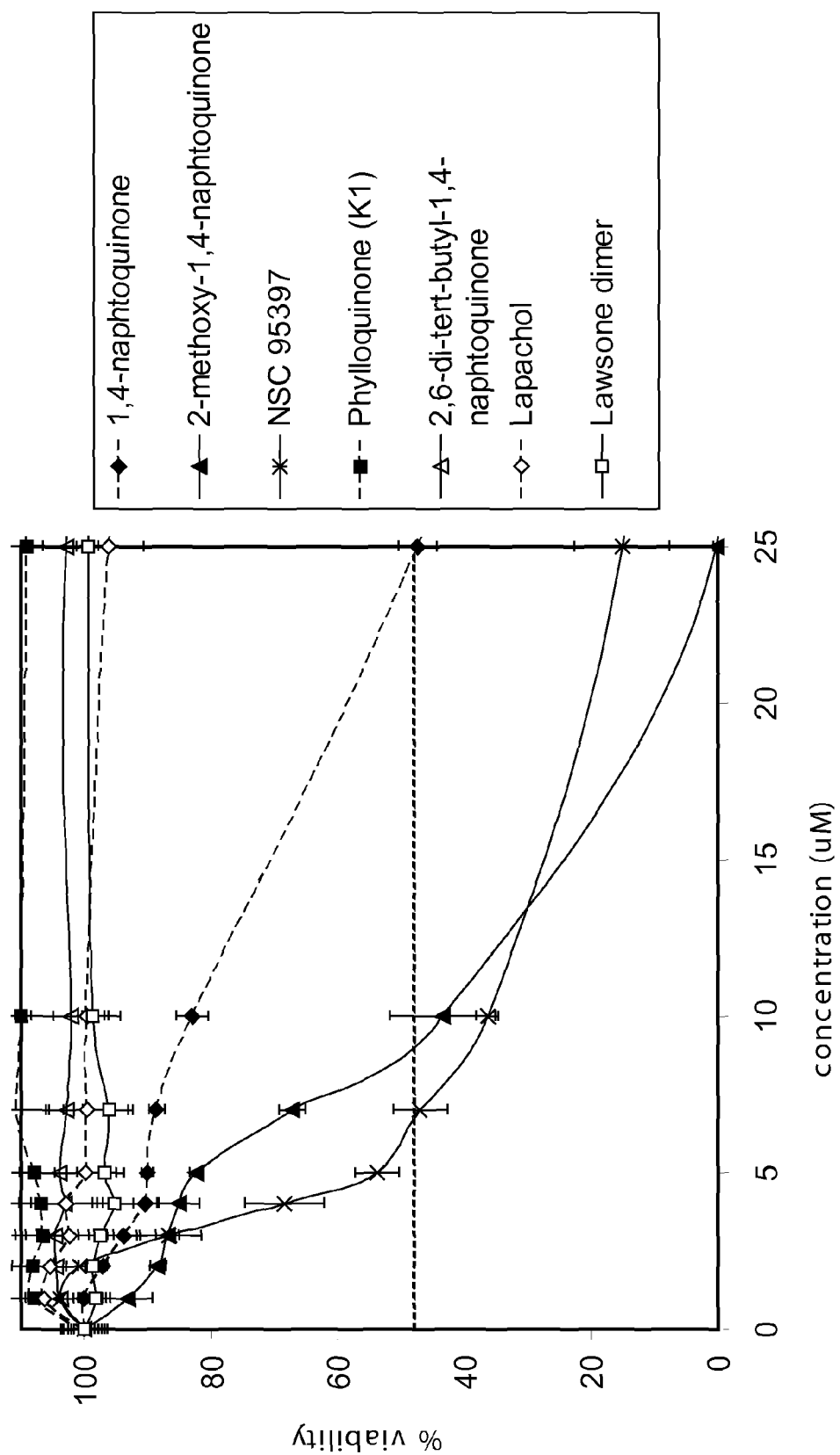
FIG. 1 shows the effect of naphthoquinone analogs on PTEN-P2/GFP cell proliferation.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, R, $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ represent substituents that can be attached to the indicated atom. An R group may be substituted or unsubstituted.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated with regard to an alkyl or alkenyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, isobutyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

The term "halogen" as used herein, means any one of the radio-stable atoms of column 7 of the Periodic Table of the Elements, such as, fluorine, chlorine, bromine and iodine.

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, amino, mono-substituted amino group and di-substituted amino group, and protected derivatives thereof.

The term "naphthoquinone analog" refers to a compound of Formula (I) wherein $R^1$, $R^2$, $R^3$, $R^4$, $R^5$, and $R^6$ are as defined herein.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, alkylamine, cyclohexylamine, triethanolamine, ethylenediamine, and salts with amino acids such as arginine and lysine.

It is understood that, in any compound described herein having one or more chiral centers, if an absolute stereochemistry is not expressly indicated, then each center may independently be of R-configuration or S-configuration or a mixture thereof. Thus, the compounds provided herein may be disatereomerically pure, disatereomerically enriched, or may be stereoisomeric mixtures. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

The term "pharmaceutical composition" refers to a mixture of a compound disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

The term "therapeutically effective amount" is used to indicate an amount of an active compound, or pharmaceutical agent, that elicits the biological or medicinal response indicated. For example, a therapeutically effective amount of compound can be the amount needed to prevent, alleviate or ameliorate symptoms of disease or prolong the survival of the subject being treated. This response may occur in a tissue, system, animal or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As used herein, the term "hormone therapy agent" refers to anti-androgens (including steroidal anti-androgens and non-steroidal anti-androgens), estrogens, luteinizing hormone-releasing hormone (LHRH) agonists, and LHRH antagonists, as well as, hormonal ablation therapy. Exemplary hormone therapy agents include, but are not limited to, cyproterone acetate, abiraterone, finasteride, flutamide, nilutamide, bicalutamide, ethylstilbestrol (DES), megestrol acetate, fosfestrol, estamustine phosphate, leuprolide, triptorelin, goserelin, histrelin, buserelin, abarelix and degarelix.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. The section below describes some of the compounds that can be used to treat cancer, or inhibit or delay the growth of cancer cells, especially prostate cancer cells alone or in combination with one or more androgen deprivation therapies (e.g., castration, hormonal castration, hormonal ablation, or hormone therapy).

II. Compounds of Formula (I)

Some embodiments disclosed herein relate to a compound of Formula (I), a pharmaceutically acceptable salt thereof, and methods of using these compounds with and without a hormone therapy agent, as described herein, to inhibit, delay, treat, or prevent prostate cancer cell growth or prostate cancer in a subject in need thereof. Formula (I):

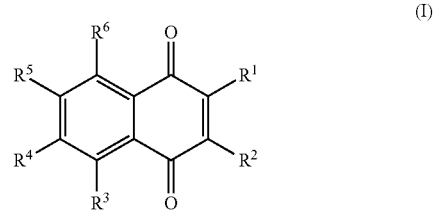

wherein: $R^1$ can be selected from hydrogen, halogen, an optionally substituted $C_{1-18}$ alkyl, an optionally substituted $C_{2-18}$ alkenyl, —$OR^7$ and —$SR^8$; $R^2$ can be selected from hydrogen, halogen, an optionally substituted $C_{1-6}$ alkyl, an optionally substituted $C_{2-6}$ alkenyl, —$OR^9$ and —$SR^{10}$; $R^3$ can be selected from hydrogen, an optionally substituted $C_{1-6}$ alkyl, and —$OR^{11}$; $R^4$ can be selected from hydrogen, an optionally substituted $C_{1-6}$ alkyl, and $OR^{12}$; $R^5$ can be selected from hydrogen, an optionally substituted $C_{1-6}$ alkyl, and —$OR^{13}$; $R^6$ can be selected from hydrogen, an optionally substituted $C_{1-6}$ alkyl, and —$OR^{14}$; and $R^7$, $R^8$, $R^9$, $R^{10}$, $R^{11}$, $R^{12}$, $R^{13}$, and $R^{14}$ can be independently selected from hydrogen and an optionally substituted $C_{1-6}$ alkyl.

In some embodiments, $R^1$ can be hydrogen. In some embodiments, $R^1$ can be halogen. In some embodiments, $R^1$ can be chloro. In some embodiments, $R^1$ can be an optionally substituted $C_{1-18}$ alkyl. Examples of optionally substituted $C_{1-18}$-alkyls include, but are not limited to, optionally substituted variants of the following: methyl, ethyl, n-propyl, isopropyl, n-butyl, isobutyl, tert-butyl, pentyl, hexyl, heptyl, octyl, nonanyl, decanyl, undecanyl, dodecanyl, tridecanyl, tetradecanyl, pentadecanyl, hexadecanyl, heptadecanyl, octadecanyl, and phytanyl. Optionally substituted $C_{1-18}$-alkyls can be branched or straight-chained. In some embodiments, $R^1$ can be an optionally substituted $C_{1-6}$ alkyl. In some embodiments, $R^1$ can be methyl. In some embodiments, $R^1$ can be t-butyl. In some embodiments, $R^1$ can be an optionally substituted $C_{2-18}$ alkenyl. Examples of optionally substituted $C_{2-18}$-alkenyls include, but are not limited to, optionally substituted variants of the following: ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, and phytenyl. Optionally substituted $C_{2-18}$-alkenyls can be branched or straight-chained, and can include one or more double bonds. In some embodiments, $R^1$ can be an optionally substituted $C_{2-6}$ alkenyl. In some embodiments, $R^1$ can be —$OR^7$, wherein $R^7$ is hydrogen. In some embodiments, $R^1$ can be —$OR^7$, wherein $R^7$ is an optionally substituted $C_{1-6}$ alkyl. In some embodiments, $R^1$ can be —$OR^7$, wherein $R^7$ is methyl. In some embodiments, $R^1$ can be —$SR^8$, wherein $R^8$ is hydrogen. In some embodiments, $R^1$ can be —$SR^8$, wherein $R^8$ is an optionally substituted $C_{1-6}$ alkyl. In some embodiments, $R^1$ can be —$SR^8$, wherein $R^8$ is $C_{1-6}$ alkyl optionally substituted with hydroxy. In some embodiments, $R^1$ can be —$SR^8$, wherein $R^8$ is —$CH_2CH_2OH$.

In some embodiments, $R^2$ can be hydrogen. In some embodiments, $R^2$ can be halogen. In some embodiments, $R^2$ can be chloro. In some embodiments, $R^2$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^2$ can be methyl. In some embodiments, $R^2$ can be an optionally substituted $C_{2-6}$ alkenyl. Examples of optionally substituted $C_{2-6}$-alkenyls include optionally substituted variants of the following: ethenyl, propenyl, butenyl, pentenyl (branched and straight-chained), and hexenyl (branched and straight-chained). In some embodiments, $R^2$ can be —$CH_2$—$CH$=$C(CH_3)_2$. In some embodiments, $R^2$ can be —$OR^9$, wherein $R^9$ is hydrogen. In some embodiments, $R^2$ can be —$OR^9$, wherein $R^9$ is an optionally substituted $C_{1-6}$ alkyl. In some embodiments, $R^2$ can be —$OR^9$, wherein $R^9$ is methyl. In some embodiments, $R^2$ can be —$SR^{10}$, wherein $R^{10}$ is hydrogen. In some embodiments, $R^2$ can be —$SR^{10}$, wherein $R^{10}$ is an optionally substituted $C_{1-6}$ alkyl. In some embodiments, $R^2$ can be —$SR^{10}$, wherein $R^{10}$ is $C_{1-6}$ alkyl optionally substituted with hydroxy. In some embodiments, $R^2$ can be —$SR^{10}$, wherein $R^{10}$ is —$CH_2CH_2OH$.

In some embodiments, $R^3$ can be hydrogen. In some embodiments, $R^3$ can be an optionally substituted $C_{1-6}$ alkyl. In some embodiments, $R^3$ can be —$OR^{11}$, wherein $R^{11}$ is hydrogen. In some embodiments, $R^3$ can be —$OR^{11}$, wherein $R^{11}$ is an optionally substituted $C_{1-6}$ alkyl.

In some embodiments, $R^4$ can be hydrogen. In some embodiments, $R^4$ can be an optionally substituted $C_{1-6}$ alkyl. In some embodiments, $R^4$ can be t-butyl. In some embodiments, $R^4$ can be —$OR^{12}$, wherein $R^{12}$ is hydrogen. In some embodiments, $R^4$ can be —$OR^{12}$, wherein $R^{12}$ is an optionally substituted $C_{1-6}$ alkyl.

In some embodiments, $R^5$ can be hydrogen. In some embodiments, $R^5$ can be an optionally substituted $C_{1-6}$ alkyl. In some embodiments, $R^5$ can be —$OR^{13}$, wherein $R^{13}$ is hydrogen. In some embodiments, $R^5$ can be —$OR^{13}$, wherein $R^{13}$ is an optionally substituted $C_{1-6}$ alkyl.

In some embodiments, $R^6$ can be hydrogen. In some embodiments, $R^6$ can be an optionally substituted $C_{1-6}$ alkyl. In some embodiments, $R^6$ can be —$OR^{14}$, wherein $R^{14}$ is hydrogen. In some embodiments, $R^6$ can be —$OR^{14}$, wherein $R^{13}$ is an optionally substituted $C_{1-6}$ alkyl.

In some embodiments, $R^7$, $R^8$, $R^9$, $R^{10}$, $R^{11}$, $R^{12}$, $R^{13}$, and $R^{14}$ can be independently selected from hydrogen. In some embodiments, $R^7$, $R^8$, $R^9$, $R^{10}$, $R^{11}$, $R^{12}$, $R^{13}$, and $R^{14}$ can be independently selected from $C_{1-6}$ alkyl. In some embodiments, $R^7$, $R^8$, $R^9$, $R^{10}$, $R^{11}$, $R^{12}$, $R^{13}$, and $R^{14}$ can be independently selected from $C_{1-6}$ alkyl, wherein the $C_{1-6}$ alkyl can be optionally substituted with a group selected from halogen, hydroxy, and $C_{1-4}$ alkyl.

In some embodiments, $R^1$ can be selected from hydrogen, halogen, an optionally substituted $C_{1-6}$ alkyl, —$OR^7$ and —$SR^8$; $R^2$ can be selected from hydrogen, halogen, an optionally substituted $C_{1-6}$ alkyl, —$OR^9$ and —$SR^{10}$; $R^3$ can be selected from hydrogen and —$OR^{11}$; $R^4$ can be selected from hydrogen and an optionally substituted $C_{1-6}$ alkyl; $R^5$ can be hydrogen; $R^6$ can be selected from hydrogen and —$OR^{14}$; and $R^7$, $R^8$, $R^9$, $R^{10}$, $R^{11}$, $R^{12}$, $R^{13}$, and $R^{14}$ can be independently selected from hydrogen and an optionally substituted $C_{1-6}$ alkyl.

In some embodiments, $R^1$, $R^2$, $R^3$, $R^4$, $R^5$ and $R^6$ can each be hydrogen. In some embodiments, $R^1$ can be methyl; $R^3$ can be —OH; and $R^2$, $R^4$, $R^5$ and $R^6$ can each be hydrogen. In some embodiments, $R^3$ and $R^6$ can each be —OH; and $R^1$, $R^2$, $R^4$ and $R^5$ can each be hydrogen. In some embodiments, $R^3$ can be —OH; and $R^1$, $R^2$, $R^4$, $R^5$ and $R^6$ can each be hydrogen. In some embodiments, $R^1$ and $R^2$ can each be —$SCH_2CH_2OH$; and $R^3$, $R^4$, $R^5$ and $R^6$ can each be hydrogen. In some embodiments, $R^1$ and $R^2$ can each be —$OCH_3$; and $R^3$, $R^4$, $R^5$ and $R^6$ can each be hydrogen. In some embodiments, $R^1$ can be —$OCH_3$; and $R^2$, $R^3$, $R^4$, $R^5$ and $R^6$ can each be hydrogen. In some embodiments, $R^1$ can be methyl; and $R^2$, $R^3$, $R^4$, $R^5$ and $R^6$ can each be hydrogen. In some embodiments, $R^1$ and $R^2$ can each be chloro; and $R^3$, $R^4$, $R^5$ and $R^6$ can each be hydrogen. In some embodiments, $R^1$ can be —OH; and $R^2$, $R^3$, $R^4$, $R^5$ and $R^6$ can each be hydrogen. In some embodiments, $R^1$ can be phytenyl; $R^2$ can be methyl; and $R^3$, $R^4$, $R^5$ and $R^6$ can each be hydrogen. In some embodiments, $R^1$ and $R^4$ can each be t-butyl; and $R^2$, $R^3$, $R^5$ and $R^6$ can each be hydrogen. In some embodiments, $R^1$ can be —OH; $R^2$ can be —$CH_2$—$CH$=$C(CH_3)_2$; and $R^3$, $R^4$, $R^5$ and $R^6$ can each be hydrogen.

In some embodiments, at least one of $R^1$, $R^2$, $R^3$, $R^4$, $R^5$ and $R^6$ cannot be hydrogen. In some embodiments, when $R^1$ is methyl; and $R^2$, $R^4$, $R^5$ and $R^6$ are each hydrogen; then $R^3$ cannot be —OH. In some embodiments, when $R^1$, $R^2$, $R^4$ and $R^5$ are each hydrogen; then at least one of $R^3$ and $R^6$ cannot be —OH. In some embodiments, when $R^1$, $R^2$, $R^4$, $R^5$ and $R^6$ are each hydrogen; then $R^3$ cannot be —OH. In some embodiments, when $R^3$, $R^4$, $R^5$ and $R^6$ are each hydrogen; then at least one of $R^1$ and $R^2$ cannot be —$SCH_2CH_2OH$. In some embodiments, when $R^3$, $R^4$, $R^5$ and $R^6$ are each hydrogen; then at least one of $R^1$ and $R^2$ cannot be —OCH$_3$. In some embodiments, when $R^2$, $R^3$, $R^4$, $R^5$ and $R^6$ are each hydrogen; then $R^1$ cannot be —OCH$_3$. In some embodiments, when $R^2$, $R^3$, $R^4$, $R^5$ and $R^6$ are each hydrogen; then $R^1$ cannot be methyl. In some embodiments, when $R^3$, $R^4$, $R^5$ and $R^6$ are each hydrogen; then at least one of $R^1$ and $R^2$ cannot be chloro. In some embodiments, when $R^2$, $R^3$, $R^4$, $R^5$ and $R^6$ are each hydrogen; then $R^1$ cannot be —OH. In some embodiments, when $R^2$ is methyl; and $R^3$, $R^4$, $R^5$ and $R^6$ are each hydrogen; then $R^1$ cannot be phytenyl. In some embodiments, when $R^2$, $R^3$, $R^5$ and $R^6$ are each hydrogen; then at least one of $R^1$ and $R^4$ cannot be t-butyl. In some embodiments, when $R^2$ is —CH$_2$—CH=C(CH$_3$)$_2$; and $R^3$, $R^4$, $R^5$ and $R^6$ are each hydrogen; then $R^1$ cannot be —OH.

Examples of compounds of Formula (I) include, but are not limited to the following:

structure of Formula (I). For example, in some embodiments, the compound of Formula (I) can be Lawsone dimer:

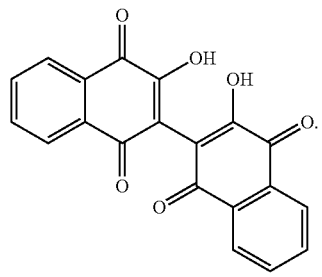 [SMILES: O=C1C(O)=C(C2=C(O)C(=O)c3ccccc3C2=O)C(=O)c2ccccc21]

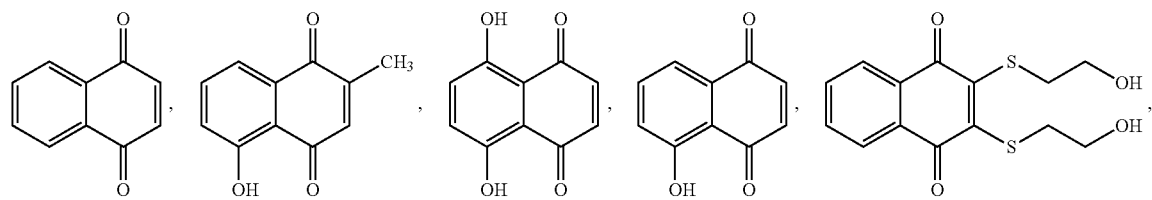

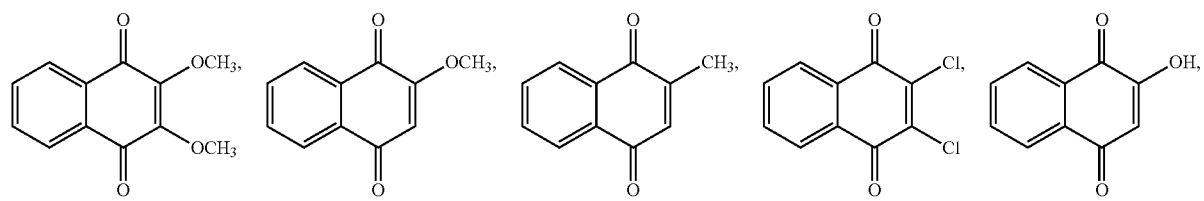

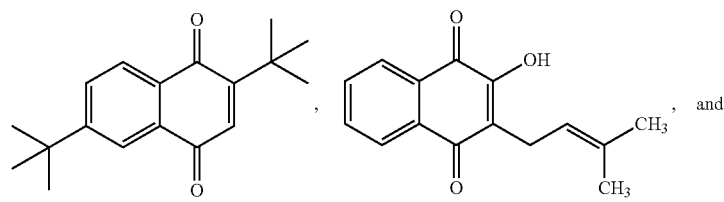

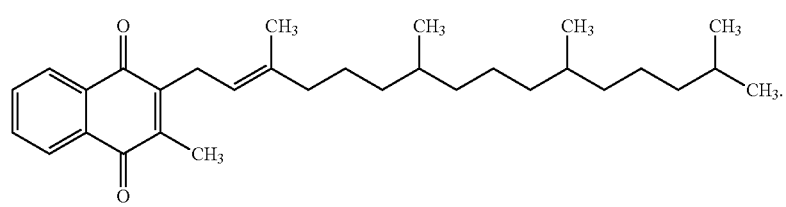

In some embodiments, the compound of Formula (I) can be a dimer, such that one of $R^1$, $R^2$, $R^3$, $R^4$, $R^5$ or $R^6$ has the The section below describes some of the conventional therapies that can be used to inhibit or delay prostate cancer cell growth and/or treat or prevent prostate cancer. It should be understood that the inventive therapies described herein can be performed with and without any of the conventional therapies for prostate cancer including any one or more of the therapies described in the following section.

III. Prostate Cancer

There were an estimated 192,280 new cases of prostate cancer diagnosed in the U.S. in 2009 and an estimated 27,360 deaths. About 90% of patients with advanced disease will develop bone metastases, associated with severe pain, loss of mobility, and spinal cord compression. Other affected organs may include the liver, lungs and brain. Advanced prostate cancer is resistant to hormone therapy, radiation and conventional chemotherapy. Although the 5-year survival rate is close to 100% for local disease, it drops to 30% for advanced cancer.

There have been some advances in the treatment of prostate cancer recently, including new surgical approaches and improvements in radiotherapy. For example:

1) In 1986, surgeons developed a technique (using da Vinci Prostatectomy) that allowed the removal of the prostate while minimizing nerve damage, thereby decreasing adverse side effects.

2) In addition, clinical researchers improved a long-established radiotherapy technique known as brachytherapy, which involves the implantation of a small amount of radioactive material (seeds) into the prostate. This radiation therapy method is an effective treatment for early-stage prostate cancer.

3) There have also been advances in hormonal therapy for prostate cancer including the development of gonadotropin-releasing hormone (GnRH) agonists, which inhibit the ability of the pituitary gland to stimulate the testes to make testosterone.

4) Advances have also been made in chemotherapy for prostate cancer. In 2004, results from two large NCI-sponsored clinical trials showed that use of the drug docetaxel could prolong the survival of men who had advanced prostate cancer which no longer responded to hormonal therapy.

Unfortunately, should the prostate-specific antigen (PSA) level remain above zero after radical prostatectomy is performed, with conventional therapy or with advanced therapy using da Vinci Prostatectomy, this indicates that the prostate cancer has spread outside the capsule, i.e., disseminated disease, and to date, there is no curable treatment for this.

Thus, all current hormonal, as well as, chemotherapy treatment regimens for such disseminated androgen dependent prostate cancers are palliative. Subsequently, even if there have been advances in the treatment of prostate cancer, finding new strategies for treatment of disseminated disease remains a crucial challenge. The section below provides more details on the use of compounds of Formula (I) to inhibit or delay the growth of cancer cells, in particular prostate cancer cells.

IV. Compounds of Formula (I) as Anticancer Agents

Compounds of Formula (I) have significant anti-cancer properties. For example, plumbagin (5-hydroxy-2-methyl-naphthalene-1,4-dione) is a naturally occurring naphthoquinone that can be found in various medicinal herbal species, including *Plumbago zeylanica*, *Statice limonium*, and *Limonium carolinianum*. Plumbagin has demonstrated anti-cancer effect toward fibrosarcomas (ED50 0.75 mg/kg body weight) and P388 lymphocytic leukemia (ED50 4 mg/kg body weight), induced regression of hepatoma, and has inhibited growth and invasion of hormone-refractory prostate cancer. Aziz et al., Cancer Res. 2008, 68(21):9024-322. Furthermore, plumbagin has shown to be a promising chemopreventive/anticarcinogenic agent against intestinal neoplasia.

Without wishing to be bound by theory, it is contemplated that the primary mechanism of cytotoxic action of plumbagin and other quinoid compounds is due to redox-cycling and electrophilic arylation. Plumbagin can be reduced by electron transfer from flavoprotein to a semiquinone radical, which can, in turn, reduce oxygen to superoxide. The resulting superoxide can consequently be converted into hydrogen peroxide, hydroxyl radicals, and/or peroxynitrite, all of which are highly reactive oxygen species (ROS) with potent cytotoxic and tumoricidial effects.

While still not wishing to be bound by theory, an additional antitumor mechanism of plumbagin and related quinones can involve direct arylation of intracellular thiols leading to depletion of glutathione (GSH). Depletion of GSH may ultimately result in alkylation of cellular macromolecules and in their inactivation. Moreover, it has been shown that low dose concentrations of plumbagin (5 umol/L) can inhibit expression of multiple molecular targets, including protein kinase Cq (PKCq), phosphatidylinositol 3-kinase (PI3K), AKT, activation of transcription factors activator protein-1 (AP-1), nuclear factor-κB (NF-κB), and signal transducer and activator of transcription 3 (Stat3) in prostate carcinoma cells. Such activities may contribute to the tumoricidial effects of plumbagin.

Studies using plumbagin in pre-clinical models have revealed that treatment with plumbagin can result in slower growth of androgen independent prostate cancer, and that the mechanism behind the slower growth may be due to apoptosis of prostate tumor cells.

It is contemplated that several compounds of Formula (I) have anti-cancer activity and that this anti-cancer activity, especially with respect to prostate cancer, can be significantly improved (e.g., synergy can be obtained) when the compounds are provided in conjunction with a blockade of testosterone/androgen/DHT (e.g., castration, a hormone treatment therapy, such as hormonal ablation). For example, it is believed that the administration of menadione (vitamin K3) to a subject in need thereof will effectively inhibit the growth of prostate cancer cells and thereby reduce the incidence of fatal prostate cancer. The combination of menadione with an antioxidant, such as ascorbic acid, alpha lipoic acid, n-acetyl cysteine (NAC), lycopene, tocpherol, tocotrienol, or others may also be beneficial. The combination of menadione and mitomycin C can also be beneficial in treating subjects with advanced solid tumors, advanced lung cancer, and advanced gastrointestinal cancer. By administering a combination of menadione and an antioxidant or plurality of antioxidants, such as vitamin C, to subjects having prostate cancer, it is contemplated that a reduction in tumor cell numbers and PSA (prostate cancer specific antigen) will be obtained.

In a phase I/IIa trial, a combination of menadione and vitamin C were given to patients with prostate cancer that had previously failed the standard of care treatment regimen (i.e., radical prostatectomy, radiotherapy and/or hormonal ablation). Ten of the patients in the trial had received hormonal ablation therapy prior to the trial but these patients were not exposed to hormonal ablation therapy at the time of receiving the combination of vitamin C and menadione. See Tareen et al., Int. J. Med. Sci, 2008, 5:62. In this study, treatment was tested in patients with late stage disease (aggressive, recurrent). It is likely that the patients that had previously received hormone therapy had become hormone-resistant at the time of the trial (which is probably why disease was progressing in these patients).

It is contemplated herein that a significantly improved inhibition of prostate cancer cell growth can be obtained when castration, hormonal castration, hormonal ablation, or hormone therapy are provided during the time a patient receives the combination of antioxidant (e.g., ascorbic acid) with a compound of Formula (I), such as, menadione. Provided herein is an improved method for treating a subject suffering from prostate cancer with a compound of Formula (I) and androgen ablation therapy to subjects with PSA values above zero after radical prostatectomy, i.e., when they have androgen-dependent disseminated disease. Today there is no cure for this and patients currently receive only palliative treatment, including hormone therapy alone. The data provided herein demonstrates that the combination of plumbagin at the time of hormone therapy is better than hormone-therapy alone.

2,3-Bis[(2-hydroxyethyl)thio]-1,4-naphthoquinone (NSC 95397) can be a potent inhibitor of the dual-specificity phosphatase Cdc25, which is involved in cell cycle regulation. NSC 95397 can inhibit the activity of mitogen-activated protein kinase phosphatases MKP-1 and MKP-3. This compound has been studied in combination with chemotherapy drugs such as doxorubicin, etoposide, oxaliplatin, and docetaxel. NSC 95397 has been studied in neuroendocrine tumor cells, human pancreatic carcinoma cells, and bronchial carcinoma cells. Furthermore, this compound has been used in prostate cancer cells so as to examine the role of the Cdc25 phosphatase in regulation of the mitogen activated protein kinase (MAP-kinase) pathway. See Nemoto et al., Prostate, 2004, 58:95. Nevertheless, the effect of NSC 95397 on the growth or survival of prostate cancer cells was not reported by Nemoto. It is contemplated that NSC 95397 can be used to inhibit prostate cancer cell growth and that a significantly improved inhibition of prostate cancer cell growth can be obtained when castration, hormonal castration, hormonal ablation, or hormone therapy are provided before, during, and/or after the time a patient receives the NSC 95397.

Juglone is believed to be a peptidyl-prolyl cis/trans isomerase (PIN-1) inhibitor. Juglone has been studied in combination with etoposide in human cancer cells and beta-lapachone can improve the effect of radiation in laryngeal epidermoid carcinoma cells. It is contemplated that the compounds of Formula (I) are highly oxidative and induce oxidative stress in cells. Accordingly, it is contemplated that juglone can be used to inhibit prostate cancer cell growth and that a significantly improved inhibition of prostate cancer cell growth can be obtained when castration, hormonal castration, hormonal ablation, or hormone therapy are provided before, during, and/or after the time a patient receives the juglone.

Naphthazarin may be a microtubule depolymerzing agent and 2,3-Dimethoxy-1,4-naphthoquinone (DMNQ) may inhibit DNA topoisomerase-I. It is contemplated that naphthazarin and/or 2,3-dimethoxy-1,4-naphthoquinone (DMNQ) can be used to inhibit prostate cancer cell growth and that a significantly improved inhibition of prostate cancer cell growth can be obtained when castration, hormonal castration, hormonal ablation, or hormone therapy are provided before, during, and/or after the time a patient receives naphthazarin and/or 2,3-dimethoxy-1,4-naphthoquinone (DMNQ).

As mentioned above, although treating a subject that has cancer (e.g., prostate cancer) with one or more compounds of Formula (I) alone or in a combination of compounds of Formula (I) can inhibit the growth of cancerous cells, a significantly improved inhibition of cancer cell growth (e.g., prostate cancer cell growth) can be obtained by providing one or more of the compounds of Formula (I), separately or in a mixture or combination, in conjunction with a therapy that reduces the androgen levels of the patient (e.g., castration, hormonal castration, hormonal ablation, or hormone therapy). That is, some embodiments include methods of inhibiting cancer cell growth (e.g., prostate cancer cell growth) or treating or preventing a cancer (e.g., prostate cancer), wherein a subject having a cancer (e.g., prostate cancer) is provided one or more compounds of Formula (I) (e.g., plumbagin) while reducing the amount of androgens in the subject (e.g., providing castration, hormonal castration, hormonal ablation, or hormone therapy). Optionally, the inhibition of cancer (e.g., prostate cancer) or a marker thereof (e.g., PSA) is evaluated after the treatment (e.g., after the combination of plumbagin and hormone therapy is provided). Stated differently, some embodiments of the invention include a combination of one or more of the compounds of Formula (I), formulated for administration separately or together, and an androgen deprivation therapy (e.g., castration, hormonal castration, hormonal ablation, or hormone therapy) for use in inhibiting or delaying the growth of prostate cancer cells or treating or preventing prostate cancer. The section below describes some of the approaches that can be used to deplete the levels of androgen in the subject so as to provide the treatments and treatment protocols described above.

V. Hormone Therapy

Hormone therapy for treating prostate cancer, or inhibiting or delaying prostate cancer cell growth, can also be called androgen deprivation therapy (ADT), chemical castration, or androgen ablation therapy. Androgens can fuel the growth of prostatic cells, including both healthy prostatic cells and cancerous prostatic cells. In some embodiments, a subject suffering from prostate cancer is provided with a hormone therapy agent that reduces the subject's androgen levels. In some embodiments, the androgen that is decreased in the subject is testosterone, dihydrotestosterone (DHT), androsterone, androstenediol, androstenedione, dehydroepiandrosterone (DHEA), and dehydroepiandrosterone sulfate (DHEA-S). In some embodiments, a subject's serum testosterone level is decreased with one or more anti-androgen agents or androgen ablation agents. Preferably, the androgen deprivation therapy is provided during a period in which one or more compounds of Formula (I) are provided.

In some embodiments, a subject suffering from prostate cancer is classified as a subject in need of a therapy for prostate cancer and said subject is provided a hormone therapy agent that reduces the subject's androgen levels while said subject is receiving one or more compounds of Formula (I), such as plumbagin, or a compound presented in Table 1. Optionally, the inhibition in prostate cancer cell growth or an inhibition in prostate cancer advancement is evaluated. Optionally, the delaying prostate cancer cell growth or delaying prostate cancer advancement is evaluated. A subject can be identified as one in need of a therapy for prostate cancer using conventional clinical pathology including, biopsy, CT scan, MRI, digital examination, Gleason score, or PSA level. Patients today also get PET scans, which are very important since they evaluate the activity of the tumor cells (glucose metabolism). Similarly, the inhibition or delay of cancer cell growth in said subject after receiving the treatment can be evaluated using conventional clinical pathology including, biopsy, CT scan, MRI, digital examination, Gleason score, or PSA level.

In some embodiments, the hormone therapy agent that can be used with any one or more of the methods or treatments described herein is selected from the group consisting of an antiandrogen (including steroidal antiandrogens and nonsteroidal antiandrogens), an estrogen, a luteinizing hormone-releasing hormone (LHRH) agonist, and a LHRH antagonist. Steroidal antiandrogen agents include, but are not limited to, cyproterone acetate and finasteride. Nonsteroidal antiandrogens include, but are not limited to, flutamide, nilutamide and bicalutamide. Estrogen agents include, but are not limited to, ethylstilbestrol (DES), megestrol acetate, fosfestrol, and estamustine phosphate. LHRH agonist agents include, but are not limited to, leuprolide, triptorelin, goserelin, histrelin and buserelin. LHRH antagonist agents include, but are not limited to, abarelix and degarelix. Desirably, one or more of the compounds selected from the group consisting of cyproterone acetate, finasteride, flutamide, abiraterone, nilutamide, bicalutamide, ethylstilbestrol (DES), megestrol acetate, fosfestrol, estamustine phosphate, leuprolide, triptorelin, goserelin, histrelin, buserelin, abarelix and degarelix are used in the methods and treatments (compositions) described herein, wherein one or more of the compounds of Formula (I) (e.g., a compound of Table 1) are provided before, during, and/or after providing said cyproterone acetate, finasteride, flutamide, abiraterone, nilutamide, bicalutamide, ethylstilbestrol (DES), megestrol acetate, fosfestrol, estamustine phosphate, leuprolide, triptorelin, goserelin, histrelin, buserelin, abarelix or degarelix.

As mentioned above, prostate cancer can be treated by hormone therapy agents, however, hormone therapy agents alone can result in the development of castration-resistant prostate cancer (CRPC). For example, hormonal therapy can initially deliver a response in a subject suffering from prostate cancer, however, the return of hormone-refractory tumors invariably prevents long-term patient survival. More effective strategies are needed to extend life expectancy and improve the quality of life for patients with advanced prostate cancer. Accordingly, some aspects of the present invention concern methods for ameliorating or inhibiting or reducing or delaying the onset of castration-resistant prostate cancer (CRPC) or treatments (e.g., compositions used for the purpose of ameliorating or inhibiting or reducing or delaying the onset of CRPC), whereby one or more of the compounds of Formula (I) (e.g., a compound from Table 1) are provided before, during and/or after providing cyproterone acetate, finasteride, abiraterone, flutamide, nilutamide, bicalutamide, ethylstilbestrol (DES), megestrol acetate, fosfestrol, estamustine phosphate, leuprolide, triptorelin, goserelin, histrelin, buserelin, abarelix or degarelix. Optionally, the inhibition in prostate cancer cell growth, an inhibition in prostate cancer advancement, or delaying the onset of CRPC is evaluated. Optionally, a patient with prostate cancer is classified as a subject in need of an agent that ameliorates, reduces, delays, or inhibits the onset of CRPC prior to receiving one or more of the combination therapies described herein. A subject can be identified as one in need of a therapy for prostate cancer using conventional clinical pathology including, biopsy, CT scan, MRI, digital examination, Gleason score, or PSA level.

Patients today also get PET scans, which are very important since they evaluate the activity of the tumor cells (glucose metabolism).

Similarly, the inhibition or delay of cancer cell growth in said subject after receiving the treatment can be evaluated using conventional clinical pathology including, biopsy, CT scan, MRI, digital examination, Gleason score, or PSA level. The section below describes the combination therapies in greater detail.

VI. Combination Therapies

In some embodiments, the compounds disclosed herein, such as a compound of Formula (I) (e.g., a compound of Table 1), or a pharmaceutically acceptable salt thereof, or a pharmaceutical composition that includes a compound described herein, can be used in combination with one or more additional agent(s). Some embodiments disclosed herein relate to a method of ameliorating or treating a neoplastic disease that can include administering to a subject suffering from a neoplastic disease a therapeutically effective amount of one or more compounds described herein (e.g., a compound of Formula (I), or a pharmaceutically acceptable salt thereof), in combination with one or more hormone therapy agents (referred to as "combination therapy"). Examples of additional agents that can be used in combination with a compound of Formula (I), or a pharmaceutically acceptable salt thereof, or a pharmaceutical composition that includes a compound of Formula (I), or a pharmaceutically acceptable salt thereof, include, but are not limited to, agents that can decrease the subject's serum androgen levels (e.g., cyproterone acetate, abiraterone, finasteride, flutamide, nilutamide, bicalutamide, ethylstilbestrol (DES), megestrol acetate, fosfestrol, estamustine phosphate, leuprolide, triptorelin, goserelin, histrelin, buserelin, abarelix or degarelix).

In an embodiment, the neoplastic disease can be cancer. In some embodiments, the neoplastic disease can be a tumor such as a solid tumor. In an embodiment, the neoplastic disease can be prostate cancer and in some embodiments the prostate cancer can be CRPC. Therefore, in some embodiments, a compound of Formula (I), or a pharmaceutically acceptable salt thereof, or a pharmaceutical composition that includes a compound of Formula (I), or a pharmaceutically acceptable salt thereof, is used in combination with one or more hormone therapy agents for the purpose of treating a subject that has prostate cancer, for inhibiting the growth of prostate cancer cells, for delaying prostate cancer, for decreasing the size of a prostate tumor, or for inhibiting the onset or development of CRPC.

In some embodiments, a compound of Formula (I), or a pharmaceutically acceptable salt thereof, or a pharmaceutical composition that includes a compound of Formula (I) (e.g., one or more of the compounds of Table 1), or a pharmaceutically acceptable salt thereof, is used in combination with surgical orchiectomy and/or one or more of the hormone therapy agents cyproterone acetate, finasteride, abiraterone, flutamide, nilutamide, bicalutamide, ethylstilbestrol (DES), megestrol acetate, fosfestrol, estamustine phosphate, leuprolide, triptorelin, goserelin, histrelin, buserelin, abarelix or degarelix such that a "combination therapy" is provided.

Normal serum testosterone ranges between 1000-300 ng/dL. In some embodiments, a subject is provided a combination therapy, as described herein, whereby a reduction in the treated subject's serum testosterone level to at least about ≤80, ≤70, ≤60, ≤50, ≤40, ≤30, ≤20, or ≤10 ng/dL is obtained. In some embodiments, a subject is provided a combination therapy that reduces the subject's serum testosterone level to at least about ≤50 ng/dL. In some embodiments, a subject is treated with a combination therapy that results in a reduction in the subject's serum testosterone level to at least about ≤20 ng/dL. In some embodiments, a subject is treated with a combination therapy, as described herein, that reduces the subject's serum testosterone level to at least about or any number in between the range of 120-70, 100-60, 80-40, 70-30, 50-20, 40-10, 30-10, or 20-10 ng/dL. In some embodiments, a subject is treated with a combination therapy that produces a reduction in the subject's serum testosterone level to about ≤95%, ≤90%, ≤80%, ≤70%, ≤60%, or ≤50% that of a healthy male. In some embodiments, a subject is treated with a combination therapy that results in a reduction in the subject's serum testosterone level to the range of at least about or any number in between the range of about 5-20%, 10-30%, 20-40%, 30-50%, 40-60%, or 50-70% that of a healthy male.

Intermittent hormonal therapy (IHT) is an alternative to continuous hormonal therapy, which may delay progression of hormone-refractory disease (i.e., CRPC). For example, intermittent therapy can be used for a period of 6 months on, followed by a period of 6 months off. In some embodiments, therapy is provided for one month on, followed by one month off. In some embodiments, therapy is provided for three months on, followed by three months off. Accordingly, one or more of the compounds of Formula (I), e.g., a compound of Table 1, can be provided before, during and/or after IHT, as described above, so as to reduce or inhibit or delay the onset of CRPC.

A non-limiting list of example combination of compounds of Formula (I), or a pharmaceutically acceptable salt thereof, or a pharmaceutical composition that includes a compound described herein, with one or more additional therapy agent(s) are provided in Tables 1 and 2. Table 1 provides a shorthand name for each compound of Formula (I) and a shorthand name for each therapy. Each numbered X compound in Table 2 has a corresponding compound structure provided in Table 1. Likewise, each numbered Y therapy in Table 2 has a corresponding therapy provided in Table 1. Therefore, each "X:Y" entry in Table 2 provides an example of a combination of a compound of Formula (I) and an therapy that can be used to treat a subject suffering from prostate cancer. For example, the combination designated as "F02:AT04" in Table 2 provides a combination of

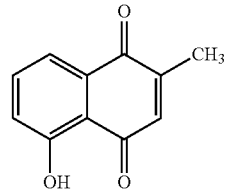

(plumbagin), and flutamide that can be used to treat a subject suffering from prostate cancer. Each of the combinations provided in Table 2 can be used with one, two, three or more additional agents described herein.

TABLE 1

| Compound of Formula (I) | | Additional Therapy | |
|---|---|---|---|
| 1,4-naphthoquinone | (F01) | cyproterone acetate | (AT01) |
| plumbagin | (F02) | finasteride | (AT02) |
| naphthazarin | (F03) | bicalutamide | (AT03) |
| juglone | (F04) | flutamide | (AT04) |

TABLE 1-continued

| Compound of Formula (I) | Additional Therapy |
|---|---|
| (F05) NSC 95397 | nilutamide (AT05) |
| (F06) DMNQ | bicalutamide. (AT06) |
| (F07) 2-methoxy-1,4-naphthoquinone | ethylstilbestrol (AT07) (DES) |
| (F08) menadione | megestrol acetate (AT08) |
| (F09) dichlon | fosfestrol (AT09) |
| (F10) lawsone | estamustine phosphate (AT10) |

TABLE 1-continued

| Compound of Formula (I) | | Additional Therapy | |
|---|---|---|---|
| 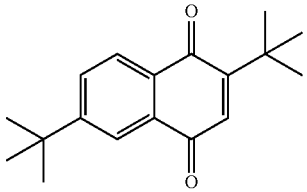 [SMILES: CC(C)(C)C1=CC(=O)c2cc(C(C)(C)C)ccc2C1=O]  2,6-di-tert-butyl-1,4-naphtoquinone | (F11) | leuprolide | (AT11) |
| lapachol | (F12) | tritorelin | (AT12) |
| phylloquinone | (F13) | goserelin | (AT13) |
| 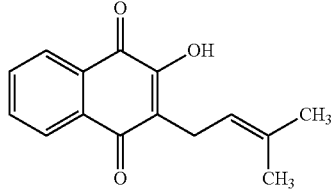 [SMILES: CC(C)=CCC1=C(O)C(=O)c2ccccc2C1=O]  lawson dimer | (F14) | histrelin | (AT14) |
| — | | buserelin | (AT15) |
| — | | abarelix | (AT16) |
| — | | degarelix | (AT17) |
| — | | surgical orchiectomy | (AT18) |

TABLE 2

| X:Y | X:Y | X:Y | X:Y | X:Y | X:Y | X:Y |
|---|---|---|---|---|---|---|
| F01:AT02 | F02:AT02 | F03:AT02 | F04:AT02 | F05:AT02 | F06:AT02 | F07:AT02 |
| F01:AT03 | F02:AT03 | F03:AT03 | F04:AT03 | F05:AT03 | F06:AT03 | F07:AT03 |
| F01:AT04 | F02:AT04 | F03:AT04 | F04:AT04 | F05:AT04 | F06:AT04 | F07:AT04 |
| F01:AT05 | F02:AT05 | F03:AT05 | F04:AT05 | F05:AT05 | F06:AT05 | F07:AT05 |
| F01:AT06 | F02:AT06 | F03:AT06 | F04:AT06 | F05:AT06 | F06:AT06 | F07:AT06 |
| F01:AT07 | F02:AT07 | F03:AT07 | F04:AT07 | F05:AT07 | F06:AT07 | F07:AT07 |
| F01:AT08 | F02:AT08 | F03:AT08 | F04:AT08 | F05:AT08 | F06:AT08 | F07:AT08 |
| F01:AT09 | F02:AT09 | F03:AT09 | F04:AT09 | F05:AT09 | F06:AT09 | F07:AT09 |
| F01:AT10 | F02:AT10 | F03:AT10 | F04:AT10 | F05:AT10 | F06:AT10 | F07:AT10 |
| F01:AT11 | F02:AT11 | F03:AT11 | F04:AT11 | F05:AT11 | F06:AT11 | F07:AT11 |
| F01:AT12 | F02:AT12 | F03:AT12 | F04:AT12 | F05:AT12 | F06:AT12 | F07:AT12 |
| F01:AT13 | F02:AT13 | F03:AT13 | F04:AT13 | F05:AT13 | F06:AT13 | F07:AT13 |

TABLE 2-continued

| X:Y | X:Y | X:Y | X:Y | X:Y | X:Y | X:Y |
|---|---|---|---|---|---|---|
| F01:AT14 | F02:AT14 | F03:AT14 | F04:AT14 | F05:AT14 | F06:AT14 | F07:AT14 |
| F01:AT15 | F02:AT15 | F03:AT15 | F04:AT15 | F05:AT15 | F06:AT15 | F07:AT15 |
| F01:AT16 | F02:AT16 | F03:AT16 | F04:AT16 | F05:AT16 | F06:AT16 | F07:AT16 |
| F01:AT17 | F02:AT17 | F03:AT17 | F04:AT17 | F05:AT17 | F06:AT17 | F07:AT17 |
| F01:AT18 | F02:AT18 | F03:AT18 | F04:AT18 | F05:AT18 | F06:AT18 | F07:AT18 |
| F08:AT02 | F09:AT02 | F10:AT02 | F11:AT02 | F12:AT02 | F13:AT02 | F14:AT02 |
| F08:AT03 | F09:AT03 | F10:AT03 | F11:AT03 | F12:AT03 | F13:AT03 | F14:AT03 |
| F08:AT04 | F09:AT04 | F10:AT04 | F11:AT04 | F12:AT04 | F13:AT04 | F14:AT04 |
| F08:AT05 | F09:AT05 | F10:AT05 | F11:AT05 | F12:AT05 | F13:AT05 | F14:AT05 |
| F08:AT06 | F09:AT06 | F10:AT06 | F11:AT06 | F12:AT06 | F13:AT06 | F14:AT06 |
| F08:AT07 | F09:AT07 | F10:AT07 | F11:AT07 | F12:AT07 | F13:AT07 | F14:AT07 |
| F08:AT08 | F09:AT08 | F10:AT08 | F11:AT08 | F12:AT08 | F13:AT08 | F14:AT08 |
| F08:AT09 | F09:AT09 | F10:AT09 | F11:AT09 | F12:AT09 | F13:AT09 | F14:AT09 |
| F08:AT10 | F09:AT10 | F10:AT10 | F11:AT10 | F12:AT10 | F13:AT10 | F14:AT10 |
| F08:AT11 | F09:AT11 | F10:AT11 | F11:AT11 | F12:AT11 | F13:AT11 | F14:AT11 |
| F08:AT12 | F09:AT12 | F10:AT12 | F11:AT12 | F12:AT12 | F13:AT12 | F14:AT12 |
| F08:AT13 | F09:AT13 | F10:AT13 | F11:AT13 | F12:AT13 | F13:AT13 | F14:AT13 |
| F08:AT14 | F09:AT14 | F10:AT14 | F11:AT14 | F12:AT14 | F13:AT14 | F14:AT14 |
| F08:AT15 | F09:AT15 | F10:AT15 | F11:AT15 | F12:AT15 | F13:AT15 | F14:AT15 |
| F08:AT16 | F09:AT16 | F10:AT16 | F11:AT16 | F12:AT16 | F13:AT16 | F14:AT16 |
| F08:AT17 | F09:AT17 | F10:AT17 | F11:AT17 | F12:AT17 | F13:AT17 | F14:AT17 |
| F08:AT18 | F09:AT18 | F10:AT18 | F11:AT18 | F12:AT18 | F13:AT18 | F14:AT18 |

The order of administration of a compound of Formula (I), or a pharmaceutically acceptable salt thereof, with one or more additional hormone therapy agent(s) can vary. In some embodiments, a compound of Formula (I), or a pharmaceutically acceptable salt thereof, can be administered prior to all additional hormone therapy agents. In other embodiments, a compound of Formula (I), or a pharmaceutically acceptable salt thereof, can be administered prior to at least one additional hormone therapy agent. In still other embodiments, a compound of Formula (I), or a pharmaceutically acceptable salt thereof, can be administered concomitantly with one or more additional hormone therapy agent(s). In yet still other embodiments, a compound of Formula (I), or a pharmaceutically acceptable salt thereof, can be administered subsequent to the administration of at least one additional hormone therapy agent. In some embodiments, a compound of Formula (I), or a pharmaceutically acceptable salt thereof, can be administered subsequent to the administration of all additional hormone therapy agents.

In some embodiments, a subject suffering from prostate cancer is treated by surgical orchiectomy (i.e., removal of the testes). In some embodiments, a compound of Formula (I), or a pharmaceutically acceptable salt thereof, can be administered after surgical orchiectomy. In some embodiments, a compound of Formula (I), or a pharmaceutically acceptable salt thereof, can be administered before and after surgical orchiectomy.

Determining and Evaluating Anti-Cancer Activity

Animal Models

Animal models are pivotal to further our understanding of the mechanisms of (progressive) growth of cancer. Currently used rodent tumor models, including transgenic tumor models, (using genetically modified mice susceptible to develop cancer), as well as implantation of human tumors under the skin in immunodeficient mice, do not sufficiently represent clinical cancer, especially with regard to metastasis and drug sensitivity. Preclinical tumor model systems employed to evaluate potential new treatment strategies should aim to represent the process and patterns of metastasis of their clinical counterparts as closely as possible.

A syngeneic pseudo-orthotopic in vivo model was developed to study the early steps of prostate cancer. Chambers are surgically placed into the dorsal skinfold of male mice. Briefly, male mice (25-30 g body weight) are anesthetized and placed on a heating pad. Two symmetrical titanium frames are implanted into the dorsal skinfold. A circular layer is excised from one of the skin layers. The underlying muscle and subcutaneous tissues are covered with a glass coverslip incorporated in one of the frames. After a recovery period of 2-3 days, stroma tissue and tumor cells are carefully placed in the chamber.

Tumor-derived cell lines can be grown directly in the chamber, corresponding to the traditional subcutaneous model. However, it was found that various minced tissues implanted in the chambers survive and revascularize, and that tumor-derived cell lines adapt to these various stroma after co-implantation, which points to this approach as an orthotopic model as well as a model for initial steps in metastasis.

For example, mouse prostate tissue can be grafted in the chamber. The graft develops its own vasculature and serve as orthotopic stroma for the tumor. A small number of prostate cancer cells (e.g., TRAMP-C2 cells derived from a TRAMP mouse) can be implanted on top of the prostate stroma. The tumor microenvironment can be important for the progression of different types of cancer, and orthotopic implantation of cancer cells can recapitulate human disease much more closely than subcutaneous implantation. Tumors can grow faster and develop better vasculature when the cancer cells are implanted into the relevant organ. Co-implanting mouse prostate cancer cells with prostate stroma can provide the tumor cells with an environment that better reflects the clinical disease compared to purely subcutaneous models. Re-vascularized stromal tissue and implanted tumors can remain viable for long periods of time using this method, for example, up to 90 days.

Phosphate and Tensin Homolog (PTEN) Deficient Model

Mouse cells derived from the PTEN (phosphatase and tensin homolog deleted in chromosome 10) deficient model of prostate cancer can be used to study prostate cancer. The tumor suppressor PTEN is one of the most frequently mutated genes in human prostate cancer. Loss of PTEN can result in constitutively high PI3-kinase and Akt activities, which may lead to increased migration, invasiveness, cell proliferation and survival. Loss of PTEN can play a major role in the pathogenesis of human prostate cancer. Alteration of at least one PTEN allele is observed in approximately 60% of primary tumors. Loss of PTEN can be associated with higher Gleason scores and poor prognosis, cancer progression toward hormone-independence, resistance to chemotherapy or to radiotherapy, and bone metastasis. PTEN-deficient mice have an increased incidence of cancer, similarly to the human genetic predisposition to cancer known as Cowden syndrome, which is caused by germline mutation in the PTEN gene. In these respects, the PTEN-deficient model appears to mimic human development quite closely. Thus, heterozygous disruption of the PTEN gene can result in spontaneous development of tumors in several tissues and prostatic intraepithelial neoplasia (PIN) lesions in the prostate. Prostate-specific homozygous loss of PTEN can be sufficient to induce prostate tumors, which can progress into metastatic disease. Heterozygous loss of PTEN, on the other hand, can cause PIN with a late latency.

Germline homozygous deletion of PTEN may result in embryonic lethality due to PTEN ablation. This can be overcome through the conditional inactivation of the gene using the Cre-LoxP system. A transgenic mouse can be generated that displays expression of the Cre recombinase specifically in the epithelial cells of the prostate through the use of the prostate-specific probasin promoter (PB-Cre4 mice). By crossing these animals with mice that have foxed PTEN alleles, it can be possible to generate both heterozygous and homozygous mice in which PTEN is deleted specifically in the prostate epithelium. Progression of prostate cancer in this model is very similar to the progression of prostate cancer as observed in humans. For example, in this model epithelial hyperplasia was observed, followed by dysplasia, PIN, invasive adenocarcinoma, and finally metastases to the lymph nodes and to the lung. Similar to human cancer, the PTEN-null mice first regress following androgen ablation, and then become androgen-independent.

Epithelial cell lines can be derived from a prostate tumor dissected from a homozygous $PTEN^{L/L}$/PBCre+ mouse. At least two clonal cell lines (PTEN-P2 and PTEN-P8) are heterozygous $PTEN^{L/+}$. The remaining allele can be silenced by forced expression of the Cre recombinase in vitro (PTEN-CaP2 and PTEN-CaP8 cells). Loss of the second allele can increase anchorage-independent growth and confer tumorigenesis in vivo. Spontaneous androgen-independence can occur in vivo, even though the PTEN-CaP2 and PTEN-CaP8 cells express the androgen receptor.

The implementation of PTEN prostate cells in the animal models disclosed herein can be highly relevant to human prostate cancer, and can allow detailed observation of the growth and/or regression of prostate tumors in response to different treatment regimens. Implantation in syngeneic mice respects many aspects of normal tumor growth. For example, two pairs of mouse prostate cancer cells (PTEN-P2/8 and PTEN-CaP2/8) can facilitate examination of metastasis in a mouse model of prostate cancer that is relevant to human cancer.

IntraVital Microscopy (IVM)

IntraVital Microscopy (IVM) can be used to visualize tumors in animals and analyze various aspects of cancer physiology such as tumor vascularization, cell migration and metastasis. An advantage of IVM includes the real-time analysis of dynamic processes with single-cell resolution. IntraVital microscopy offers the possibility to follow tumor growth in a non-invasive, non-destructive manner. The application of IVM can be limited to animal models that bear visually accessible tumors. Therefore, the dorsal skinfold chamber model described above can be compatible with IVM. Using IVM can permit a number of parameters to be measured in living animals and as a function of time, including tumor growth, angiogenesis, infiltration by immune cells, tumor cell migration, mitosis (cell-division) and apoptosis (programmed cell death), all in the context of the host and in real time.

VIII. Pharmaceutical Compositions

Some embodiments described herein relates to a pharmaceutical composition, that can include a therapeutically effective amount of one or more compounds described herein (e.g., a compound of Formula (I), (e.g., a compound in Table 1) or a pharmaceutically acceptable salt thereof, and/or a hormone therapy agent) and a pharmaceutically acceptable carrier, diluent, excipient or combination thereof. In some embodiments, the pharmaceutical composition can include a single diastereomer of a compound of Formula (I), or a pharmaceutically acceptable salt thereof, (for example, a single diastereomer is present in the pharmaceutical composition at a concentration of greater than 99% compared to the total concentration of the other diastereomers). In other embodiments, the pharmaceutical composition can include a mixture of diastereomers of a compound of Formula (I), or a pharmaceutically acceptable salt thereof. For example, the pharmaceutical composition can include a concentration of one diastereomer of >about 50%, ≥60%, ≥70%, ≥80%, ≥90%, ≥95%, or ≥98%, as compared to the total concentration of the other diastereomers. In some embodiments, the pharmaceutical composition includes a racemic mixture of diastereomers of a compound of Formula (I), or a pharmaceutically acceptable salt thereof.

Some embodiments described herein relates to a pharmaceutical composition, that can include a therapeutically effective amount a compound of Formula (I), an additional hormone therapy agent, and a pharmaceutically acceptable carrier, diluent, excipient or combination thereof. Some embodiments described herein relates to a pharmaceutical composition, that can include a therapeutically effective amount a compound of Formula (I), and a pharmaceutically acceptable carrier, diluent, excipient or combination thereof. Some embodiments relate to a pharmaceutical composition that can include a therapeutically effective amount of a hormone therapy agent and a pharmaceutically acceptable carrier, diluent, excipient or combination thereof.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound and/or agent exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound and/or agent in a local rather than systemic manner, for example, via injection of the compound directly into the infected area, often in a depot or sustained release formulation. Furthermore, one may administer the compound and/or agent in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound and/or agent described herein formulated in a compatible pharmaceutical carrier may also be prepared, placed in an appropriate container, and labeled for treatment of an indicated condition.

IX. Dosing

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, an active ingredient will be administered for a period of continuous therapy, for example for a week or more, or for months or years. In some embodiments, an active ingredient can be administered one time per day.

Multiple doses of an active ingredient can be administered to a subject. For example, an active ingredient can be administered once per month, twice per moth, three times per month, every other week (qow), once per week (qw), twice per week (biw), three times per week (tiw), four times per week, five times per week, six times per week, every other day (qod), daily (qd), twice a day (qid), or three times a day (tid), over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

In some embodiments, a compound of Formula (I) or a pharmaceutically acceptable salt thereof, and a hormone therapy agent can be cyclically administered to a patient. Cycling therapy involves the administration of a first active ingredient for a period of time, followed by the administration of a second active ingredient for a period of time and repeating this sequential administration. Cycling therapy can reduce the development of resistance to one or more therapies, avoid or reduce the side effects of one or more therapies, and/or improve the efficacy of treatment. In some embodiments, a compound of Formula (I) or a pharmaceutically acceptable salt thereof, and a hormone therapy agent are administered in a cycle of less than about 3 weeks, about once every two weeks, about once every 10 days, or about once every week. The number of cycles can be from about 1 to about 12 cycles, or from about 2 to about 10 cycles, or from about 2 to about 8 cycles.

In some embodiments, the active ingredient can be a compound of Formula (I), or a pharmaceutically acceptable salt thereof. In some embodiments, the active ingredient can be a hormone therapy agent. In some embodiments, both an active ingredient of compound of Formula (I), or a pharmaceutically acceptable salt thereof, and an active ingredient of a hormone therapy agent are administered to a subject.

The daily dosage regimen for an adult human patient may be the same or different for two active ingredients provided in combination. For example, a compound of Formula (I) can be provided at a dose of between 0.01 mg and 3000 mg, while a hormone therapy agent can be provided at a dose of between 1 mg and 700 mg. The dosage or each active ingredient can be, independently, a single one or a series of two or more given in the course of one or more days, as is needed by the subject. In some embodiments, the active ingredients will be administered for a period of continuous therapy, for example for a week or more, or for months or years. In some embodiments, a compound of Formula (I), or a pharmaceutically acceptable salt thereof, can be administered one time per day. In some embodiments, the hormone therapy agent can be administered once a week.

In instances where human dosages for active ingredients have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the active ingredients disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each active ingredient but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Active ingredients disclosed herein can be evaluated for efficacy and toxicity using known methods. For example, the toxicology of a particular active ingredient, or of a subset of the active ingredients, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular active ingredient may be established using several recognized methods, such as in vitro methods, animal models, or human clinical trials. When selecting a model to determine efficacy, the skilled artisan can be guided by the state of the art to choose an appropriate model, dose, route of administration and/or regime.

EXAMPLES

Additional embodiments are disclosed in further detail in the following examples, which are not in any way intended to limit the scope of the claims.

Example 1

Compounds of Formula (I) can be prepared by methods known in the art. Additionally, many compounds of Formula (I) are naturally occurring organic compounds that can be isolated from plants. Furthermore, many compounds of Formula (I) are commercially available.

Plumbagin is soluble in alcohol, acetone, chloroform, benzene, and acetic acid. Plumbagin has been used in preparation with Ethanol (in vitro) and in preparation with DMSO (in vitro) or DMSO with PEG 30% (in vivo).

Example 2

Cell Culture:
PTEN-P2/GFP cells that stably express histone H2B-GFP fusion protein. Kanda et al. (Kanda T, Sullivan K F, Wahl G M. *Histone-GFP fusion protein enables sensitive analysis of chromosome dynamics in living mammalian cells. Curr Biol* 1998 Mar. 26; 8(7):377-85) developed a highly sensitive method for observing chromosome dynamics in living cells. They fused the human Histone H2B gene to the gene encoding the GFP, which was transfected into human HeLa cells to generate a stable line constitutively expressing H2B-GFP. The H2B-GFP fusion protein was incorporated into chromatin without affecting cell cycle progression. We have generated cDNA encoding a Histone H2B-GFP fusion protein under the 5'LTR in the LXRN retroviral cassette, and have introduced it into a number of human as well as murine cancer cell lines by retroviral transduction.

Cells are grown in DMEM medium containing 10% FBS, 2 mM L-glutamine, 100 U/ml penicillin/100 µg/ml streptomycin, insulin-selenium-transferrin (5 µg/ml insulin), and DHT $10^{-8}$M final. Androgen withdrawal is achieved by keeping the cells in phenol red-free DMEM medium containing 10% charcoal-treated FBS and the same supplements as in the normal medium except for DHT. Cells are maintained in a humidified incubator at 37° C. and 5% $CO_2$. G418 (100 µg/ml) is added to maintain stable expression of H2B-GFP.

Cell Counting:
Cells in 12-well plates are washed once with PBS, detached using Trypsin, and transferred to a suspension vial in a final volume of 10 ml PBS. Cells are counted using a COULTER™ Multisizer II instrument (Beckman Coulter Inc., Hialeah, Fla.) gated for the appropriate cell size and corrected for particulate debris.

Animal Model and Surgical Techniques:
Animal experiments have been approved as appropriate. All surgical procedures are performed in a sterile laminar flow hood. Dorsal skinfold chambers and surgical instruments are autoclaved before use. Saline used to keep tissue moist during surgical preparation is mixed with gentamicin (50 µl/ml).

Male Nude mice (25-35 g body weight) are anesthetized (7.3 mg ketamine hydrochloride and 2.3 mg xylazine/100 g body weight, i.p.) and placed on a heating pad. Two symmetrical titanium frames are implanted into a dorsal skinfold, so as to sandwich the extended double layer of skin. A 15 mm full thickness circular layer is excised. The underlying muscle (*M. cutaneous* max.) and subcutaneous tissues are covered with a glass coverslip incorporated in one of the frames. After a recovery period of 2-3 days, prostate tissue and cancer cell spheroids are carefully placed in the chamber. Small circular Band Aids are applied on the backside of the chamber after surgery to prevent scratching. Before surgery, Buprenorphine (0.1 mg/kg) will be given IP. After surgery Meloxicam will be given in the drinking water for 4 days Meloxicam (5.0 mg/ml), is added at 35 µl per 100 ml of water to be medicated.

Preparation of Stroma:
A male donor mouse is euthanized and the anterior prostate tissue is excised, put in a Petri dish with antibiotics (gentamicin 50 µl/ml), and minced with fine scissors into small pieces (<1 $mm^2$) for implantation.

Preparation of Tumor Spheroids:
Liquid overlay plates are generated using 1% Agarose melted in DMEM that is added to round-bottom 96-well plates (50 ul/well). Cancer cells grown as pre-confluent monolayers are trypsinized, diluted to a final volume of 250, 000 tumor cells/ml. Viability is determined using Trypan blue. The cells are plated at 100 ul/well into the agarose-coated plates. After 48 hrs the cells form spheroids, which are picked and washed in serum-free medium before implantation into the mouse chambers. Viability is determined using Trypan blue. The size of the implanted spheroid can be determined precisely to minimize variations between animals.

Surgical Castration:
Mice are anesthetized with 7.3 mg ketamine hydrochloride and 2.3 mg xylazine/100 g body weight, i.p. A lateral incision across the scrotum is made and the testes are individually ligated and excised. The wound was cauterized. The incision was then sutured and sealed with Nexaband® acrylic.

Intravital Microscopy:
Fluorescence microscopy is performed using a Mikron Instrument Microscope equipped with epi-illuminator and video-triggered stroboscopic illumination from a xenon arc (MV-7600, EG&G). A silicon intensified target camera (SIT68, Dage-MTI) is attached to the microscope. A Hamamatsu image processor (Argus 20) with firmware version 2.50 (Hamamatsu Photonic System) is used for image enhancement and for the capture of images to a computer. A Zeiss Plan Neoflour 1.25×/0.035 objective is used to obtain an over-view of the chamber and to determine tumor size. A Zeiss A-Plan 10×/0.25 objective is used to capture images for calculation of vascular parameters. A Zeiss Achroplan 20×/0.5 W objective is used to capture images for calculation of mitotic and apoptotic indices. Our system permits evaluation of the following parameters.

Tumor Area ($A_T$) is defined as number of pixels with photo density above 75 (256 gray levels), i.e., $A_T = \Sigma A_k$, for 75<k<255.

Number of Tumor Cells:

When tumors are heterogeneous, changes in $A_T$ do not directly reflect tumor growth. An estimate of the number of tumor cells ($N_{TC}$) can be obtained by fitting to a quadratic function of an intensity index, e.g. $N_{TC} = -3.296 \times 10^{-12} + 190.6 \times I_T + 7.7310^{-2} \times (I_T)^2$, where the index of intensity is given by $I_T = \Sigma A_k * k$, for 75<k<255.

Mitotic and Apoptotic Indices:

At each time point, two peripheral and two central ×20 fields of the tumor are captured with a FITC filter and an integrated frame grabber. Only mitotic figures in metaphase-telophase (MI) are included in the mitotic indices to exclude the potential artifact of nuclear membrane distortion. Apoptotic/Pyknotic nuclei are defined as $H_2B$-GFP labeled nuclei with a cross sectional area <30 µm². Nuclear karyorrhexis (NK), easily distinguishable by the vesicular nuclear condensation and brightness of H2BGFP, is included within this apoptotic indices.

Image Analysis of Vascular Parameters:

For each spheroid, video recordings are used to calculate length, area and vascular density of the neovasculature being induced by the implanted tumor spheroids. Vascular parameters are analyzed from the video recording using Image-Pro Plus. Photomicrographs obtained with the ×10 objective, are "flattened" to reduce the intensity variations in the background pixels. An Area of Interest (AOI) is selected to eliminate distorted areas, and thresholding is used to segment the picture into objects and background. This panel is used to calculate the vascular area ($A_V$). The picture is skeletonized to calculate the vascular length ($L_V$). The average tumor vessel diameter $D_V$ is calculated as $A_V/L_V$, and the vascular density ($\Delta_V$) is calculated as $L_V$ per tumor area. Finally, we calculate the growth rate of the total area of tumor vasculature.

Example 3

Effect of Naphthoquinone Analogs on PTEN-P2/GFP Cell Proliferation

Figure 2:
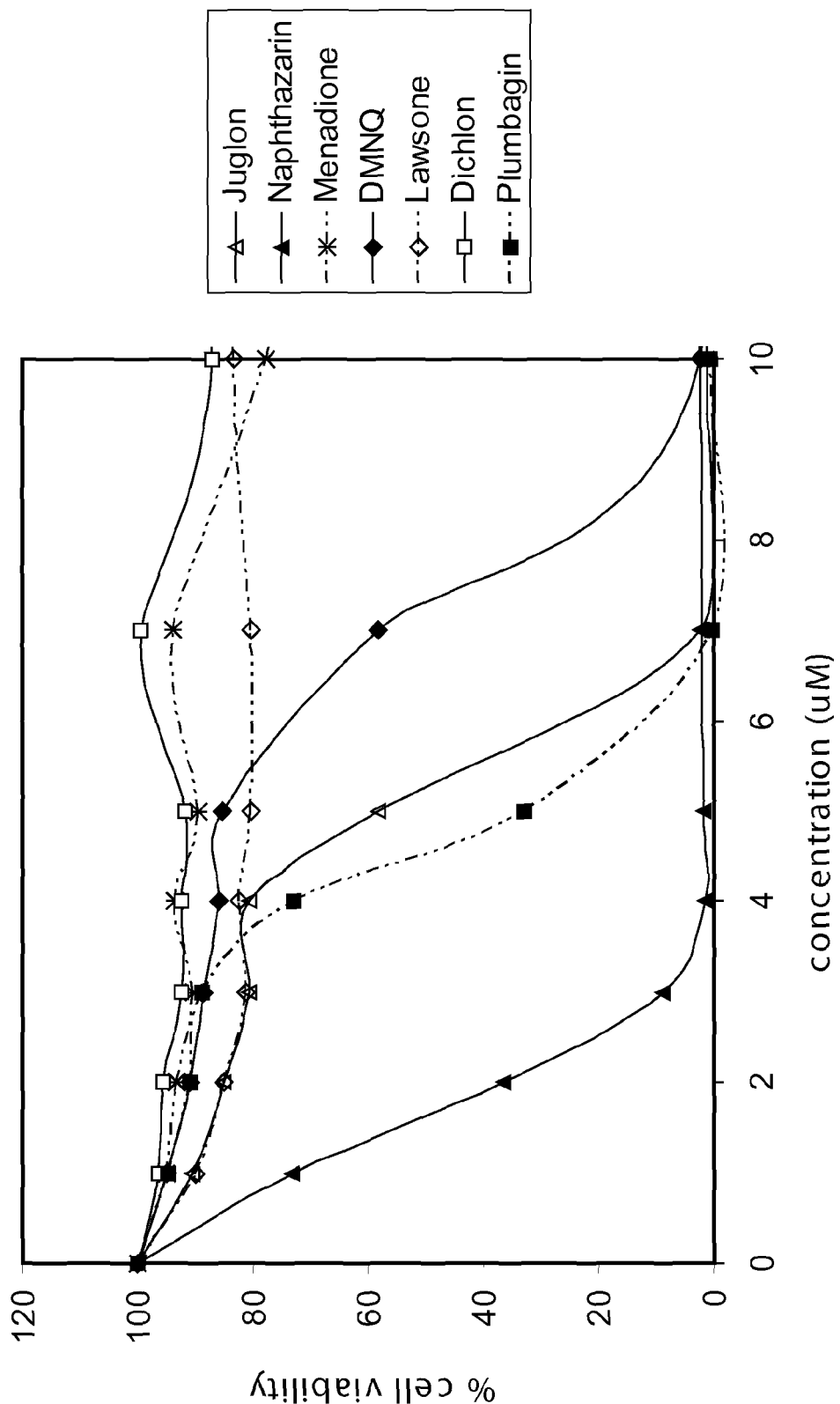
FIG. 2 shows the effect of naphthoquinone analogs on PTEN-P2/GFP cell proliferation.

PTEN-P2/GFP prostate cancer cells were plated at a density of 8000 cells/well in 96-well plates (triplicates) in growing medium containing 10% Fetal Bovine Serum and DHT. The next day, increasing concentrations of a naphthoquinone analog (diluted from 10 mM DMSO stock solutions) were incubated for 24 hrs. Cell viability was determined by the formazan-based cytotoxicity assay "CellTiter96Aqueous nonradioactive proliferation assay" (Promega). The results are shown in Tables 3 and 4, and FIGS. 1 and 2.

TABLE 3

| conc (µM) | 1,4-naphtoquinone % viability | σ | 2-methoxy-1,4-naphtoquinone % viability | σ | NSC 95397 % viability | σ | Phylloquinone (K1) % viability | σ |
|---|---|---|---|---|---|---|---|---|
| 0 | 100.0 | 3.6 | 100.0 | 2.2 | 100.0 | 3.7 | 100.0 | 2.7 |
| 1 | 100.0 | 3.3 | 93.1 | 3.9 | 103.7 | 5.6 | 107.9 | 6.1 |
| 2 | 97.0 | 0.7 | 88.4 | 1.3 | 100.6 | 4.4 | 108.1 | 5.2 |
| 3 | 93.9 | 2.6 | 86.9 | 1.9 | 86.6 | 5.1 | 106.4 | 7.1 |
| 4 | 90.4 | 1.8 | 85.0 | 3.2 | 68.4 | 6.3 | 106.8 | 8.1 |
| 5 | 90.1 | 0.9 | 82.5 | 1.0 | 53.8 | 3.5 | 108.0 | 6.8 |
| 7 | 88.7 | 1.3 | 67.2 | 2.2 | 47.1 | 4.3 | 110.8 | 7.5 |
| 10 | 83.0 | 2.5 | 43.5 | 8.2 | 36.3 | 1.7 | 110.1 | 9.2 |
| 25 | 47.3 | 3.0 | 0.3 | 0.4 | 15.1 | 7.5 | 109.1 | 7.4 |
| 50 | 0.1 | 0.5 | -0.4 | 0.2 | 4.8 | 1.0 | 109.8 | 8.2 |

| conc (µM) | 2,6-di-tert-butyl-1,4-naphtoquinone % viability | σ | Lapachol % viability | σ | Lawsone dimer % viability | σ | Juglone % viability | σ |
|---|---|---|---|---|---|---|---|---|
| 0 | 100.0 | 1.7 | 100.0 | 3.2 | 100.0 | 2.1 | 100.0 | 3.0 |
| 1 | 103.9 | 3.0 | 106.4 | 6.2 | 98.3 | 2.4 | 90.7 | 2.7 |
| 2 | 104.5 | 4.7 | 105.3 | 6.1 | 98.6 | 2.3 | 85.1 | 3.1 |
| 3 | 104.7 | 6.3 | 102.4 | 7.0 | 97.4 | 3.6 | 80.6 | 3.6 |
| 4 | 103.0 | 7.2 | 102.8 | 5.6 | 95.1 | 2.9 | 80.5 | 1.2 |
| 5 | 104.0 | 6.3 | 99.8 | 4.8 | 96.8 | 3.1 | 58.2 | 6.0 |
| 7 | 102.8 | 2.7 | 99.7 | 6.5 | 96.1 | 3.7 | 2.3 | 2.3 |
| 10 | 102.2 | 6.2 | 99.6 | 5.4 | 98.6 | 1.7 | 1.1 | 0.5 |
| 25 | 102.9 | 3.6 | 96.2 | 5.6 | 99.4 | 1.8 | 2.5 | 0.2 |
| 50 | 92.9 | 6.0 | 86.1 | 4.4 | 97.9 | 1.8 | 5.3 | 1.9 |

TABLE 3-continued

| conc (μM) | Naphthazarin % viability | σ | Menadione % viability | σ | DMNQ % viability | σ | Lawsone % viability | σ |
|---|---|---|---|---|---|---|---|---|
| 0 | 100.0 | 3.6 | 100.0 | 2.5 | 100.0 | 3.3 | 100.0 | 3.4 |
| 1 | 73.4 | 5.6 | 95.0 | 3.1 | 95.0 | 3.9 | 90.1 | 1.3 |
| 2 | 36.4 | 2.6 | 93.1 | 1.8 | 91.0 | 1.5 | 85.1 | 1.9 |
| 3 | 8.9 | 4.6 | 90.2 | 3.7 | 88.5 | 2.1 | 81.3 | 3.5 |
| 4 | 1.5 | 0.7 | 93.5 | 1.7 | 85.9 | 3.4 | 82.5 | 3.5 |
| 5 | 1.7 | 0.6 | 89.4 | 3.7 | 85.3 | 7.9 | 80.4 | 3.5 |
| 7 | 2.2 | 0.6 | 94.0 | 2.0 | 58.3 | 4.2 | 80.3 | 2.9 |
| 10 | 2.4 | 0.9 | 77.5 | 7.0 | 2.4 | 1.8 | 83.1 | 1.9 |
| 25 | 5.4 | 0.7 | 2.4 | 0.7 | 0.9 | 0.6 | 87.0 | 2.4 |
| 50 | 9.1 | 0.5 | 2.9 | 0.7 | 0.8 | 0.5 | 96.0 | 1.5 |

| conc (μM) | Dichlon % viability | σ | Plumbagin % viability | σ |
|---|---|---|---|---|
| 0 | 100.0 | 3.3 | 100.0 | 0.8 |
| 1 | 96.5 | 2.0 | 94.6 | 2.2 |
| 2 | 95.6 | 1.7 | 90.9 | 3.3 |
| 3 | 92.3 | 3.6 | 88.9 | 2.1 |
| 4 | 92.2 | 2.3 | 73.0 | 0.7 |
| 5 | 91.8 | 1.7 | 32.9 | 6.0 |
| 7 | 99.3 | 4.2 | 0.4 | 0.4 |
| 10 | 87.1 | 1.1 | 0.6 | 0.2 |
| 25 | 89.2 | 3.0 | — | — |
| 50 | 4.9 | 2.3 | — | — |

TABLE 4

| Compound | IC50(μM) |
|---|---|
| Naphtazarin | 1.65 |
| Plumbagin | 4.55 |
| Juglone | 5.3 |
| NSC 95397 | 6.2 |
| DMNQ | 7.35 |
| 2-methoxy-1,4-naphtoquinone | 8.95 |
| Menadione | 14.5 |
| 1,4-naphtoquinone | 24.1 |
| Dichlon | 37.75 |
| Phylloquinone (K1) | >50 |
| 2,6-di-tert-butyl-1,4-naphtoquinone | >50 |
| Lapachol | >50 |
| Lawson | >50 |
| Lawsone dimer | >50 |

Example 4

Dose Response Plumbagin in PTEN-P2/GFP Cells

Figure 3:
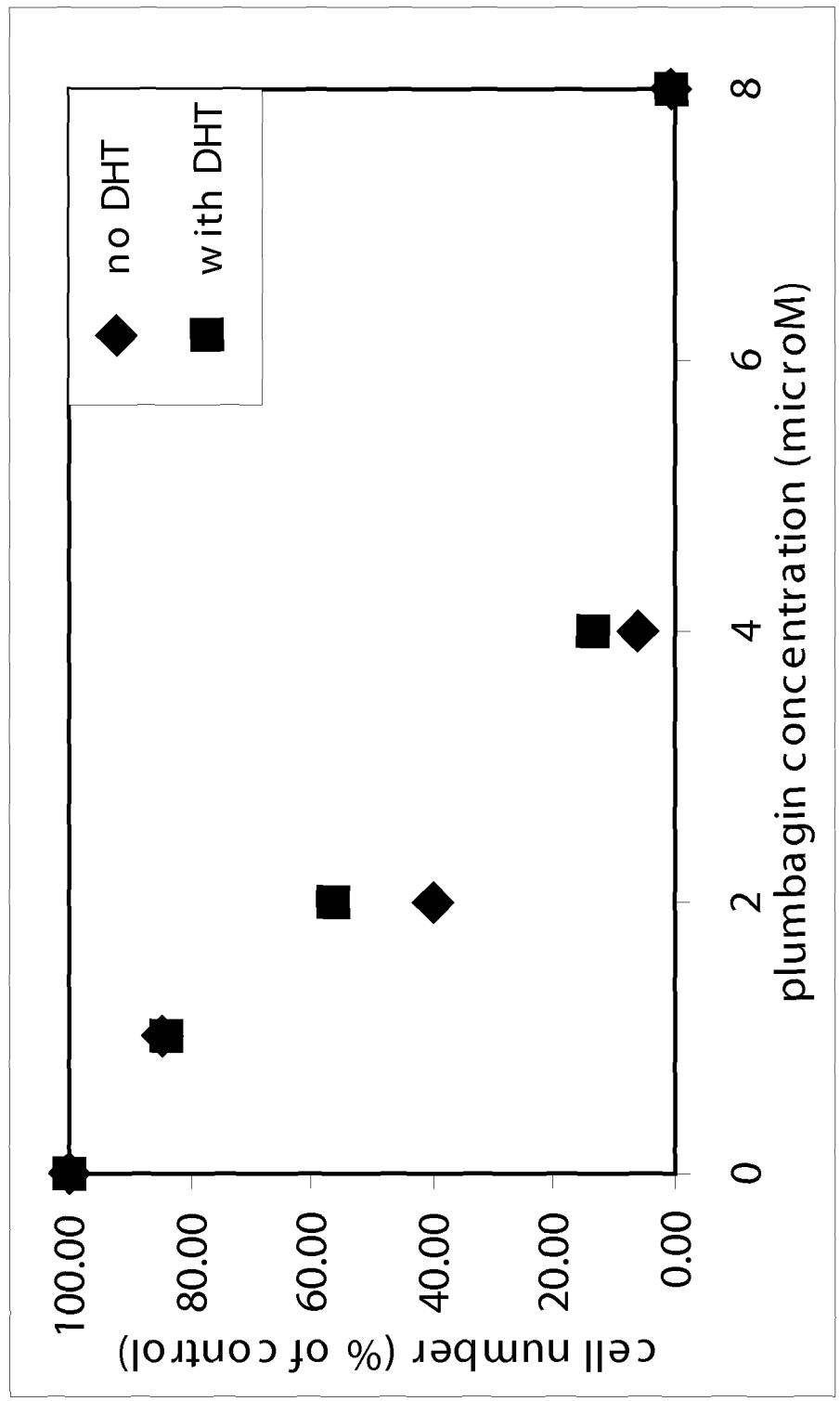
FIG. 3 shows the dose response of plumbagin in PTEN-P2/GFP cells.

PTEN-P2/GFP mouse cancer cells were placed in androgen withdrawal medium in the presence or absence of DHT (dihydrotestosterone) at a final concentration of $10^{-8}$ M. Plumbagin was added at the indicated concentrations for 24 hours. The absence of DHT simulates surgical or chemical castration. Cells were trypsinized and counted using a Cell Coulter counter Multisizer II, which excludes debris. Results represent cell numbers as percent of control (in which the number of cells in the absence of drug is 100%). FIG. 3 is a graph that shows the mean of two separate experiments, each run in duplicates. The results are shown in Table 5 and FIG. 3. The results indicate that in vitro, the combination treatment of plumbagin with simulated surgical or chemical castration was more efficient than treatment with plumbagin alone.

Androgen withdrawal medium: DMEM high-glucose phenol-red free, with the following additives: 10% charcoal-treated Fetal Bovine Serum, 25 μg/ml bovine pituitary extract, 5 μg/ml insulin, 6 ng/ml EGF recombinant.

TABLE 5

| μM plumbagin | % control | % control | Average |
|---|---|---|---|
| | no DHT | | |
| 0 | 100.01 | 100.00 | 100.00 |
| 1 | 73.70 | 95.96 | 84.83 |
| 2 | 42.90 | 37.14 | 40.02 |
| 4 | 10.12 | 1.57 | 5.84 |
| 8 | 0.45 | 0.22 | 0.33 |
| | with DHT | | |
| 0 | 100.00 | 100.00 | 100.00 |
| 1 | 106.93 | 61.29 | 84.11 |
| 2 | 94.18 | 19.16 | 56.67 |
| 4 | 22.62 | 4.89 | 13.76 |
| 8 | 0.85 | 0.40 | 0.62 |

Example 5

In Vivo Effect of Plumbagin Combined with Castration in the Pseudo-Orthotopic Chamber Model for Prostate Cancer Platinum chambers were placed in the dorsal skinfold of nude mice by surgery. Two days later, minced prostate tissue from BalbC mice (syngeneic) was grafted into the chambers and allowed to vascularize for 7 to 10 days. Small tumor cells spheroids were implanted into each chamber. Tumor cells PTEN-P2 stably transfected with H2B-GFP fusion protein (PTEN-P2/GFP) were used in these experiments. When tumor vascularization was established (about 5-7 days), the animals were surgically castrated to inhibit androgen production. Surgical castration induces androgen deprivation, and is known in the art to effectively mimic clinical hormone therapy. The mice were treated with plumbagin soon after castration. Plumbagin administration schedule was 1 mg/kg (DMSO and PEG30%) via intraperitoneal injection, once/day. The results unexpectedly indicate that the combination treatment of plumbagin with castration was more efficient in vivo than either treatment alone. Therefore, this experiment provides an important indication that castration (whether surgical or chemical) in combination with plumbagin can provide a significant improvement over therapies that were previously known in the art.

Furthermore, the results demonstrate that treatment with castration only, or treatment with plumbagin only, did not lead to a marked decrease in tumor size. However, the combination treatment of castration with plumbagin unexpectedly resulted in significant decreases in tumor size. As such, the combination therapies described herein provide significant improvements in treating prostate cancer over therapies that were previously known in the art.

Figure 4:
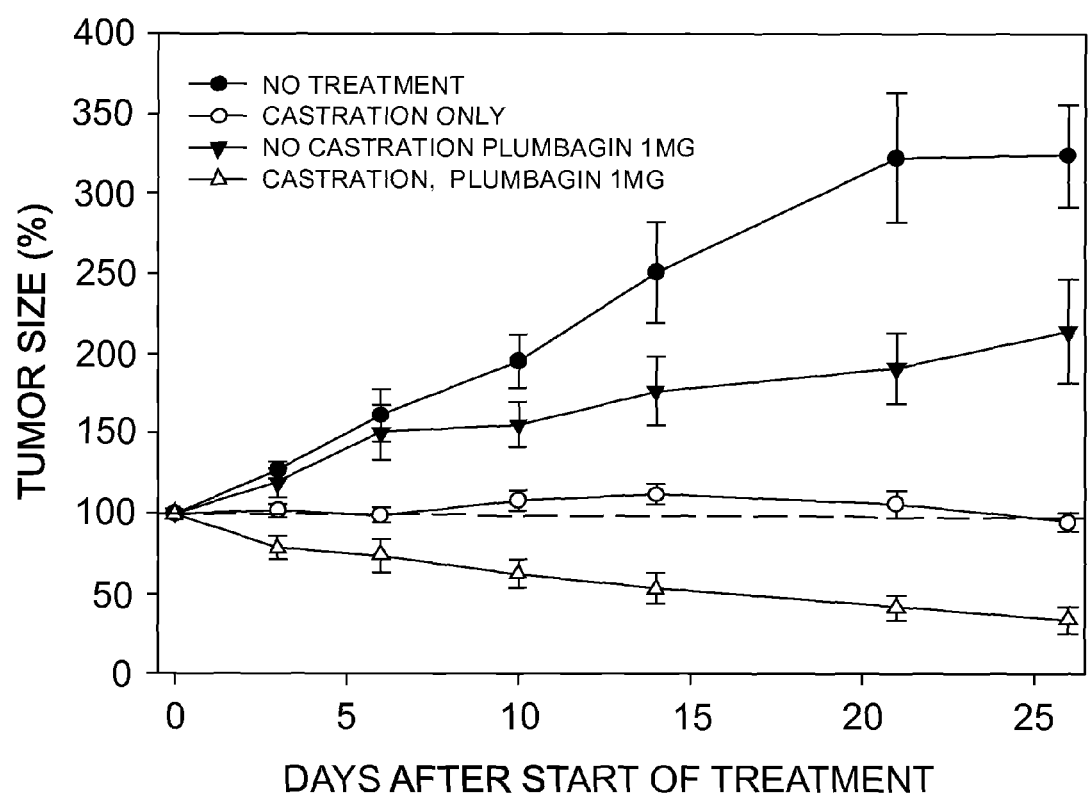
FIG. 4 compares the growth of tumors without treatment, with castration alone, with plumbagin alone, and the combination of castration and plumbagin.

FIG. 4 compares the growth of tumors without treatment, castration alone, plumbagin alone, and the combination of castration and plumbagin.

Figure 5:
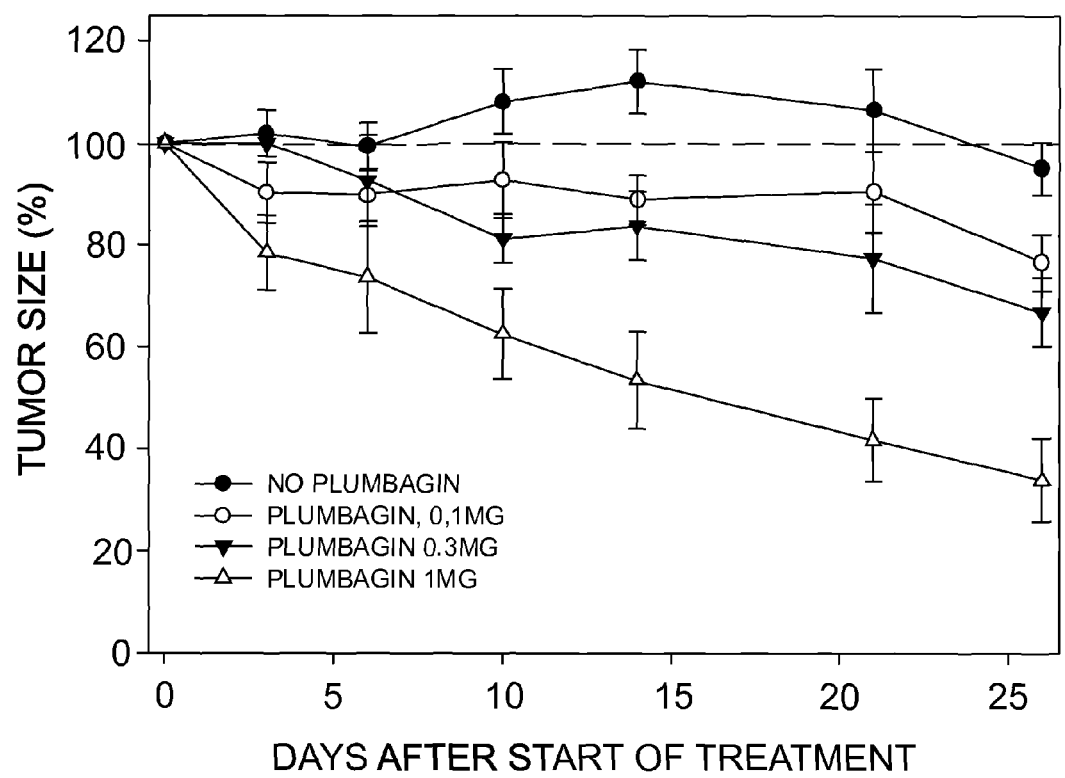
FIG. 5 shows the effect of plumbagin at 0.1 mg/kg, 0.3 mg/kg and 1 mg/kg, given in combination with castration.

FIG. 5 shows the effect of plumbagin at 0.1 mg/kg, 0.3 mg/kg and 1 mg/kg, given in combination with castration. In FIGS. 4 and 5, day 0 is the first day of plumbagin treatment.

Example 6

In Vivo Effect of Plumbagin Combined with Castration in the Pseudo-Orthotopic Chamber Model for Prostate Cancer Platinum chambers were placed in the dorsal skinfold of nude mice by surgery. Two days later, minced prostate tissue from BalbC mice (syngeneic) was grafted into the chambers and allowed to vascularize for 7 to 10 days. Small tumor cells spheroids were implanted into each chamber. Tumor cells PTEN-P2 stably transfected with H2B-GFP fusion protein (PTEN-P2/GFP) were used in these experiments. The animals were surgically castrated about three weeks after implantation to inhibit androgen production. Surgical castration induces androgen deprivation, and is known in the art to effectively mimic clinical hormone therapy. Two weeks after castration, the mice were treated daily with plumbagin at 2 mg/kg ip.

Figure 6:
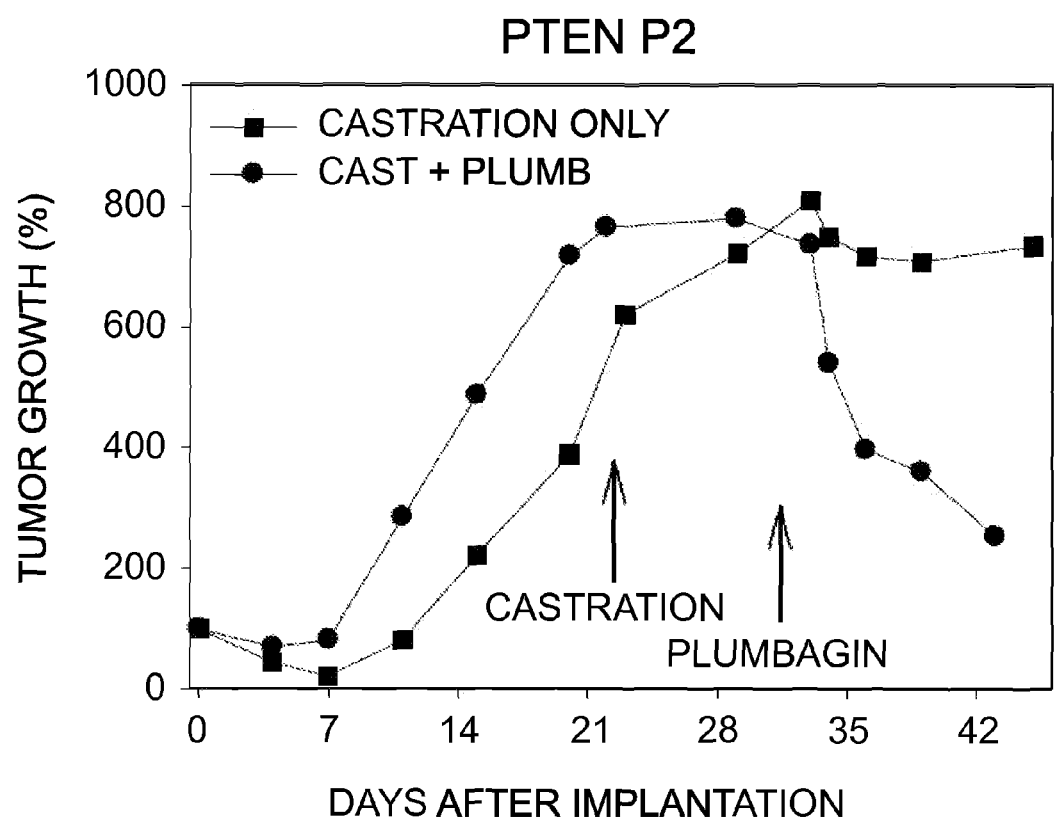
FIG. 6 illustrates the effect of adding plumbagin after surgical castration.

FIG. 6 illustrates the effect of adding plumbagin after surgical castration.

Figure 7:
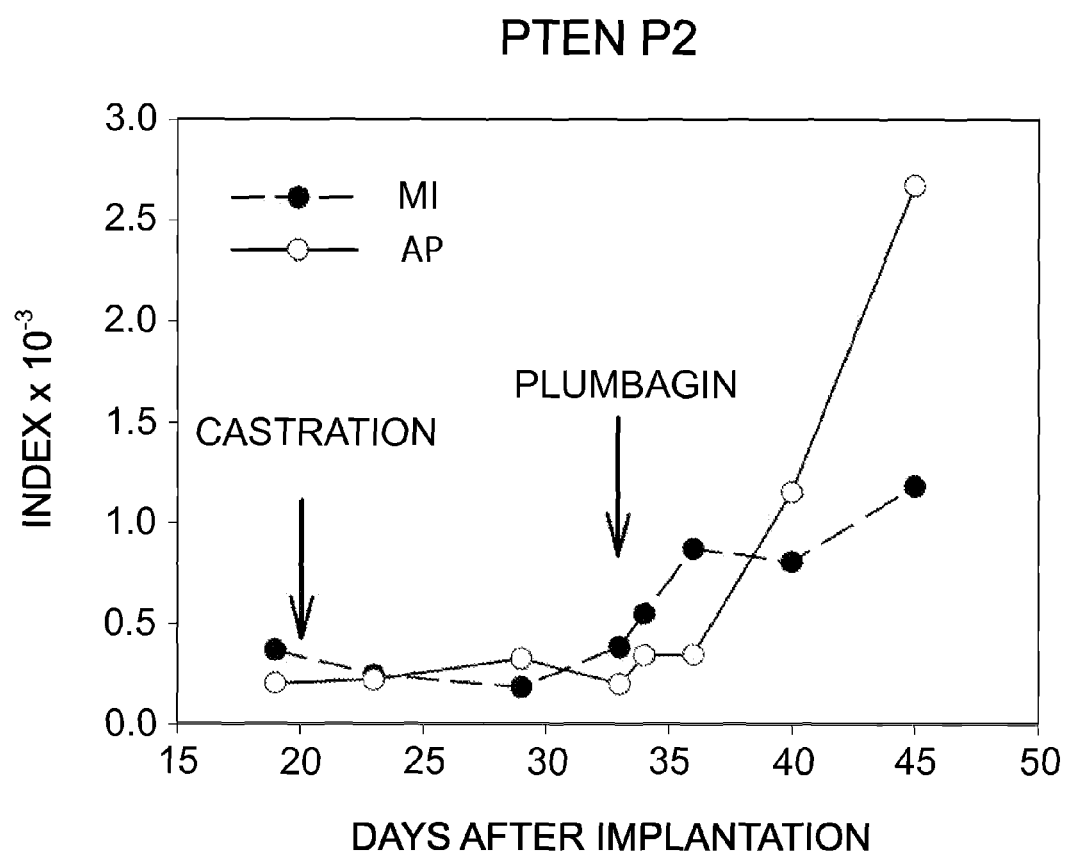
FIG. 7 illustrates increasing apoptosis (AP) and mitosis (MI) after daily administration of plumbagin ip (2 mg/kg).

FIG. 7 illustrates increasing apoptosis (AP) and mitosis (MI) after daily administration of plumbagin ip (2 mg/kg). This figure illustrates that underlying the rapid tumor regression, there was an increase in apoptosis, but also that mitosis increased, which was interpreted as cell cycle arrest.

The results unexpectedly indicate that the combination treatment of plumbagin with castration was more efficient in vivo than castration alone. Therefore, this experiment provides an important indication that castration (whether surgical or chemical) in combination with plumbagin can provide a significant improvement over therapies that were previously known in the art.

Furthermore, the results demonstrate that treatment with castration only, did not lead to a marked decrease in tumor size. However, the combination treatment of castration with plumbagin unexpectedly resulted in significant decreases in tumor size. As such, the combination therapies described herein provide significant improvements in treating prostate cancer over therapies that were previously known in the art.

Without wishing to be bound by theory, the observations indicate that tumor regression is likely caused by a combination of decreased vascularization due to androgen withdrawal, together with tumor cell growth arrest or with tumor cells apoptosis due mostly to plumbagin treatment. Thus, the efficacy of the combination was much better in vivo than can be observed in vitro because the separate effects of each treatment on distinct biological compartments (vasculature stroma possibly inflammatory cells) are not represented in the culture of cell lines.

Example 7

Dose Response Plumbagin in Human LNCaP Cells

LNCaP hormone-sensitive human prostate cancer cells were placed in androgen withdrawal medium in the absence of DHT (dihydrotestosterone). The absence of DHT simulates surgical or chemical castration. The androgen withdrawal medium was phenol-red free DMEM high-glucose containing 10% charcoal-treated Fetal Bovine Serum.

Figure 8:
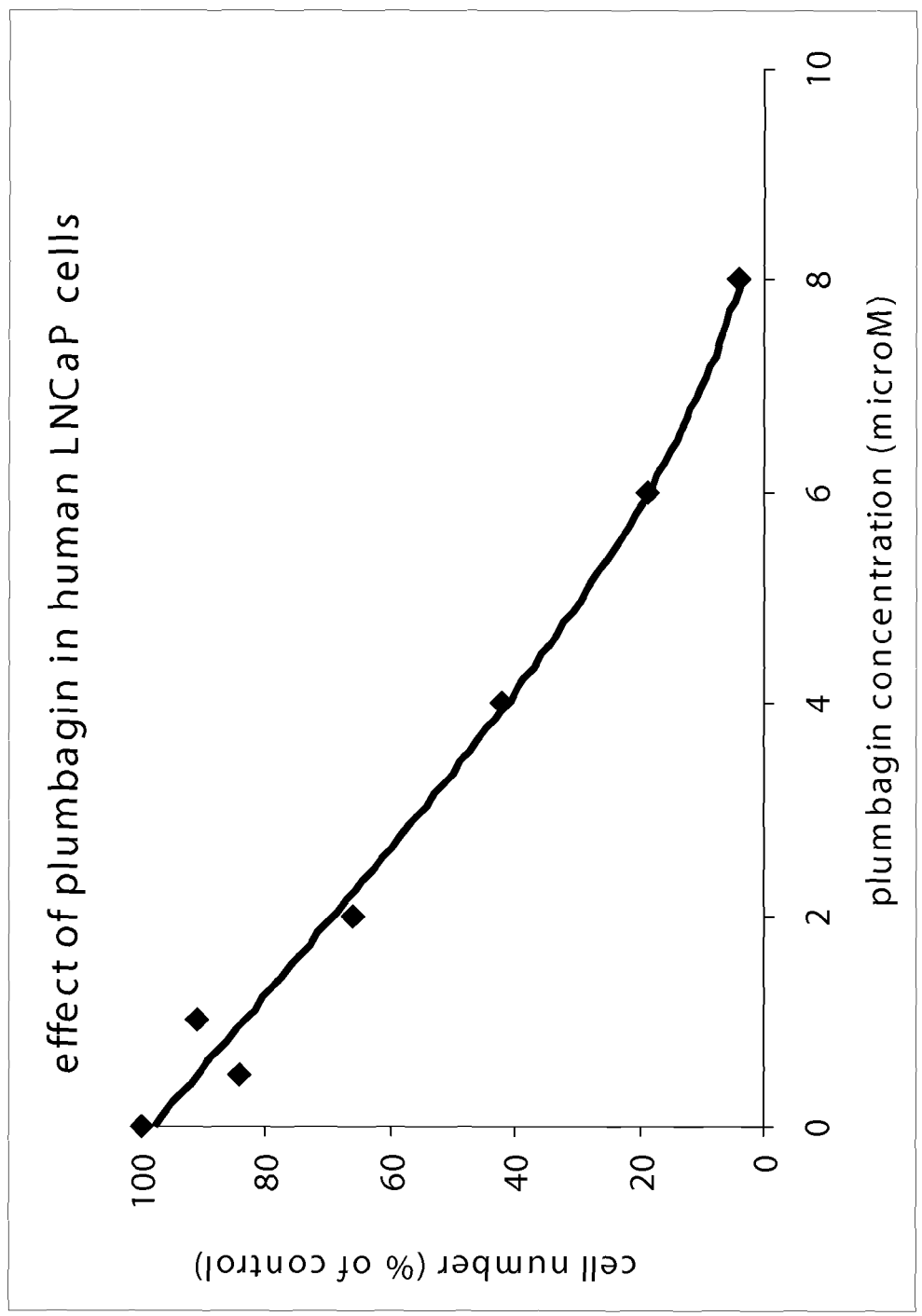
FIG. 8 illustrates the effect of plumbagin in human LNCaP cells in the absence of dihydrotestosterone.

Plumbagin was added at the indicated concentrations in Table 6 for 24 hours. Cells were trypsinized and counted using a Cell Coulter counter Multisizer II, which excludes debris. The results in Table 6 represent cell numbers as percent of control (in which the number of cells in the absence of drug is 100%). FIG. 8 illustrates the effect of plumbagin in human LNCaP cells. The results indicate that in vitro, the combination treatment of plumbagin with simulated surgical or chemical castration is more efficient than treatment castration alone.

TABLE 6

| Plumbagin conc. | cell number/20 | | | | | | | | % |
|---|---|---|---|---|---|---|---|---|---|
| (µM) | trial 1 | trial 2 | trial 3 | trial 4 | trial 5 | trial 6 | trial 7 | mean | control |
| 0 | 7245 | 7376 | 7551 | 7603 | 7327 | 8047 | 7562 | 7530 | 100 |
| 0.5 | 6422 | 5989 | 6453 | 6475 | — | — | — | 6335 | 84.13 |
| 1 | 6997 | 7139 | 6769 | 6490 | — | — | — | 6849 | 90.95 |
| 2 | 5324 | 5282 | 4522 | 4821 | — | — | — | 4987 | 66.23 |
| 4 | 3005 | 3082 | 3327 | 3300 | — | — | — | 3179 | 42.21 |
| 6 | 1396 | 1500 | 1323 | 1352 | — | — | — | 1393 | 18.50 |
| 8 | 330 | 283 | 284 | 287 | — | — | — | 296 | 3.93 |

Example 8

In Vivo Effect of Plumbagin Combined with Chemical Castration

Platinum chambers are placed in the dorsal skinfold of nude mice by surgery. Two days later, minced prostate tissue from BalbC mice (syngeneic) are then grafted into the chambers and allowed to vascularize for 7 to 10 days. Small tumor cells spheroids are then implanted into each chamber. Tumor cells PTEN-P2 stably transfected with H2B-GFP fusion protein (PTEN-P2/GFP) are then used in these experiments. When tumor vascularization is established (about 5-7 days), the animals are treated with an antiandrogen compound (e.g., cyproterone acetate) to induce androgen deprivation. The mice are then treated with plumbagin or an analog thereof (e.g., a compound from Table 1). Plumbagin or analog thereof is administered according to the schedule: 1 mg/kg (DMSO and PEG30%) via intraperitoneal injection, once/day. Control mice that are not treated with cyproterone acetate are analyzed in parallel. Also, mice treated with cyproterone acetate, but not treated with plumbagin are analyzed in parallel. The results will show that the combination of plumbagin (or analog thereof) with the antiandrogen compound (e.g., cyproterone acetate) will inhibit prostate cancer cell growth more efficiently than treatment with plumbagin (or analog thereof) or antiandrogen compound (e.g., cyproterone acetate) alone.

It will be understood by those of skill in the art that numerous and various modifications can be made without departing from the spirit of the present disclosure. Therefore, it should be clearly understood that the forms disclosed herein are illustrative only and are not intended to limit the scope of the present disclosure.

What is claimed is:

1. A method of inhibiting or delaying the growth of prostate cancer, comprising administering to a subject having prostate cancer a therapeutically effective amount of a compound of Formula (I) or a pharmaceutically acceptable salt of Formula (I):

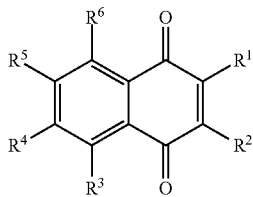

(I)

wherein:
$R^1$ is methyl;
$R^2$ is hydrogen;
$R^3$ is —OH;
$R^4$ is hydrogen;
$R^5$ is hydrogen;
$R^6$ is hydrogen; and
wherein the compound of Formula (I) is administered to the subject in combination with, subsequent to, or concomitantly with, an androgen deprivation therapy that reduces the production of testosterone; and wherein the growth of prostate cancer is inhibited or delayed.

2. The method of claim 1, wherein the androgen deprivation therapy is surgical orchiectomy.

3. The method of claim 1, wherein the androgen deprivation therapy is administration of a luteinizing hormone-releasing hormone (LHRH) agonist or a LHRH antagonist.

4. The method of claim 1, wherein the androgen deprivation therapy is administration of a compound selected from the group consisting of leuprolide, triptorelin, goserelin, abarelix, degarelix, and abiraterone.

5. The method of claim 1, wherein the androgen deprivation therapy decreases the subject's serum testosterone level to about 5-20% of a healthy male subject.

6. The method of claim 1, wherein said method inhibits the growth of prostate cancer.

7. The method of claim 1, wherein said method inhibits or delays the onset of castration-resistant prostate cancer.

8. The method of claim 1, wherein the androgen deprivation therapy is abiraterone.

9. The method of claim 1, wherein the androgen deprivation therapy is leuprolide.

10. The method of claim 1, wherein the androgen deprivation therapy is degarelix.

11. The method of claim 1, wherein the compound of formula (I) is administered to the subject orally.

12. The method of claim 1, wherein the androgen deprivation therapy is administered to the subject orally.

13. The method of claim 1, wherein the compound of formula (I) and the androgen deprivation therapy are administered to the subject orally.

14. The method of claim 1, wherein said prostate cancer is androgen dependent prostate cancer.

15. The method of claim 1, wherein said prostate cancer is castration-resistant prostate cancer.

16. The method of claim 1, wherein the androgen deprivation therapy decreases the subject's serum testosterone level to at least about ≤50 ng/dL.

17. The method of claim 1, wherein the androgen deprivation therapy decreases the subject's serum testosterone level to at least about ≤20 ng/dL.

18. The method of claim 1, wherein the method results in a decrease in prostate cancer tumor size.

* * * * *